(12) United States Patent
Nair et al.

(10) Patent No.: US 10,189,899 B2
(45) Date of Patent: Jan. 29, 2019

(54) USE OF A CD6 BINDING PARTNER AND METHOD BASED THEREON

(71) Applicant: BIOCON LIMITED, Bangalore (IN)

(72) Inventors: Pradip Nair, Bangalore (IN); Ramakrishnan Melarkode, Bangalore (IN); Bala S. Manian, Los Altos Hills, CA (US); Abhijit Barve, Bangalore (IN); Usha Bughani, Bangalore (IN); Jose Enrique Montero Casimiro, Havana (CU)

(73) Assignee: BIOCON LIMITED, Bangalore (IN)

( * ) Notice: Subject to any disclaimer, the term of this patent is extended or adjusted under 35 U.S.C. 154(b) by 0 days.

(21) Appl. No.: 14/905,506

(22) PCT Filed: Jul. 23, 2014

(86) PCT No.: PCT/IB2014/063345
§ 371 (c)(1),
(2) Date: Jan. 15, 2016

(87) PCT Pub. No.: WO2015/011658
PCT Pub. Date: Jan. 29, 2015

(65) Prior Publication Data
US 2016/0152705 A1    Jun. 2, 2016

(30) Foreign Application Priority Data

Jul. 23, 2013 (IN) .......................... 3264/CHE/2013

(51) Int. Cl.
*C07K 16/28* (2006.01)
*G01N 33/564* (2006.01)
*A61K 39/00* (2006.01)

(52) U.S. Cl.
CPC .......... *C07K 16/28* (2013.01); *C07K 16/2896* (2013.01); *G01N 33/564* (2013.01); *A61K 2039/505* (2013.01); *C07K 2317/76* (2013.01); *G01N 2333/7155* (2013.01)

(58) Field of Classification Search
None
See application file for complete search history.

(56) References Cited

U.S. PATENT DOCUMENTS

| | | |
|---|---|---|
| 699,755 A | 5/1902 | Hoag |
| 5,604,209 A | 2/1997 | Ubasawa et al. |
| 5,712,120 A | 1/1998 | Rodriguez et al. |
| 6,162,432 A | 12/2000 | Wallner et al. |
| 6,221,907 B1 | 4/2001 | Balasubramanian |
| 6,267,958 B1 | 7/2001 | Andya et al. |
| 6,372,215 B1 | 4/2002 | Starling et al. |
| 6,572,857 B1 | 6/2003 | Casimiro et al. |
| 8,435,521 B2 | 5/2013 | Casimiro et al. |
| 8,524,233 B2 | 9/2013 | Melarkode et al. |
| 9,217,037 B2 | 12/2015 | Melarkode et al. |
| 9,670,285 B2 | 6/2017 | Melarkode et al. |
| 10,000,573 B2 | 6/2018 | Melarkode et al. |
| 2002/0187526 A1 | 12/2002 | Ruben et al. |
| 2003/0113316 A1 | 6/2003 | Kaisheva et al. |
| 2004/0091490 A1 | 5/2004 | Johnson et al. |
| 2004/0197324 A1 | 10/2004 | Liu et al. |
| 2006/0173170 A1 | 8/2006 | Chamberlain et al. |
| 2006/0210557 A1 | 9/2006 | Luisi et al. |
| 2007/0086979 A1 | 4/2007 | Chevrier et al. |
| 2010/0047242 A1 | 2/2010 | Casimiro et al. |
| 2010/0092423 A1 | 4/2010 | Casimiro et al. |
| 2010/0166767 A1* | 7/2010 | Presta ................ C07K 16/2866 424/158.1 |
| 2011/0002939 A1* | 1/2011 | Melarkode ......... C07K 16/2896 424/154.1 |
| 2012/0231009 A1 | 9/2012 | Ramini et al. |
| 2014/0031529 A1 | 1/2014 | Melarkode et al. |
| 2016/0024220 A1 | 1/2016 | Casimiro et al. |
| 2016/0168256 A1 | 6/2016 | Melarkode et al. |
| 2017/0066835 A1 | 3/2017 | Casimiro et al. |
| 2017/0281808 A1 | 10/2017 | Melarkode et al. |

FOREIGN PATENT DOCUMENTS

| | | |
|---|---|---|
| CN | 101199483 B | 1/2011 |
| EP | 0807125 A2 | 11/1997 |
| EP | 0807125 B1 | 10/2004 |
| EP | 2119452 | 11/2009 |
| ES | 2192128 | 9/2003 |
| ES | 2254174 T3 | 6/2006 |
| WO | WO 1995/012614 A1 | 5/1995 |
| WO | WO 1997/004801 A1 | 2/1997 |
| WO | WO 1997/019111 A2 | 5/1997 |
| WO | WO 1998/003551 A1 | 1/1998 |
| WO | WO 1998/047531 A2 | 10/1998 |
| WO | WO199843089 | 10/1998 |
| WO | WO 2000/067796 A1 | 11/2000 |
| WO | WO 2001/070984 A2 | 9/2001 |
| WO | WO 2001/091793 A1 | 12/2001 |
| WO | WO 2005/080432 A2 | 9/2005 |
| WO | WO 2007/147001 A2 | 12/2007 |
| WO | WO 2008/071394 A1 | 6/2008 |
| WO | WO 2008/077355 A1 | 7/2008 |
| WO | WO 2008/077356 A1 | 7/2008 |
| WO | WO 2008/086395 A2 | 7/2008 |
| WO | WO 2008/157409 A1 | 12/2008 |
| WO | WO 2009/002521 A2 | 12/2008 |
| WO | WO 2009/037190 A2 | 3/2009 |
| WO | WO2009113083 | 9/2009 |
| WO | WO 2011/061712 A1 | 5/2011 |
| WO | WO 2015/011658 A1 | 1/2015 |

OTHER PUBLICATIONS

Brucklacher-Waldert et al. (Brain 2009: 132; 3329-3341).*

(Continued)

*Primary Examiner* — Zachary S Skelding

(57) ABSTRACT

The present disclosure relates to methods for treatment and prevention of disease conditions mediated by T-helper 17 (Th17) and/or T-helper 1 (Th1) T lymphocytes (T cells). In particular, the present disclosure relates to use of anti-CD6 antibody for treatment of disease conditions mediated by auto-reactive Th17 and Th1 T lymphocytes. The methods of the present disclosure further have utility in methods for modulating an immune response by suppressing production of the cytokine IL-23R, thereby decreasing inflammation mediated by Th17 cells.

6 Claims, 7 Drawing Sheets

(56) References Cited

OTHER PUBLICATIONS

Figure 1:
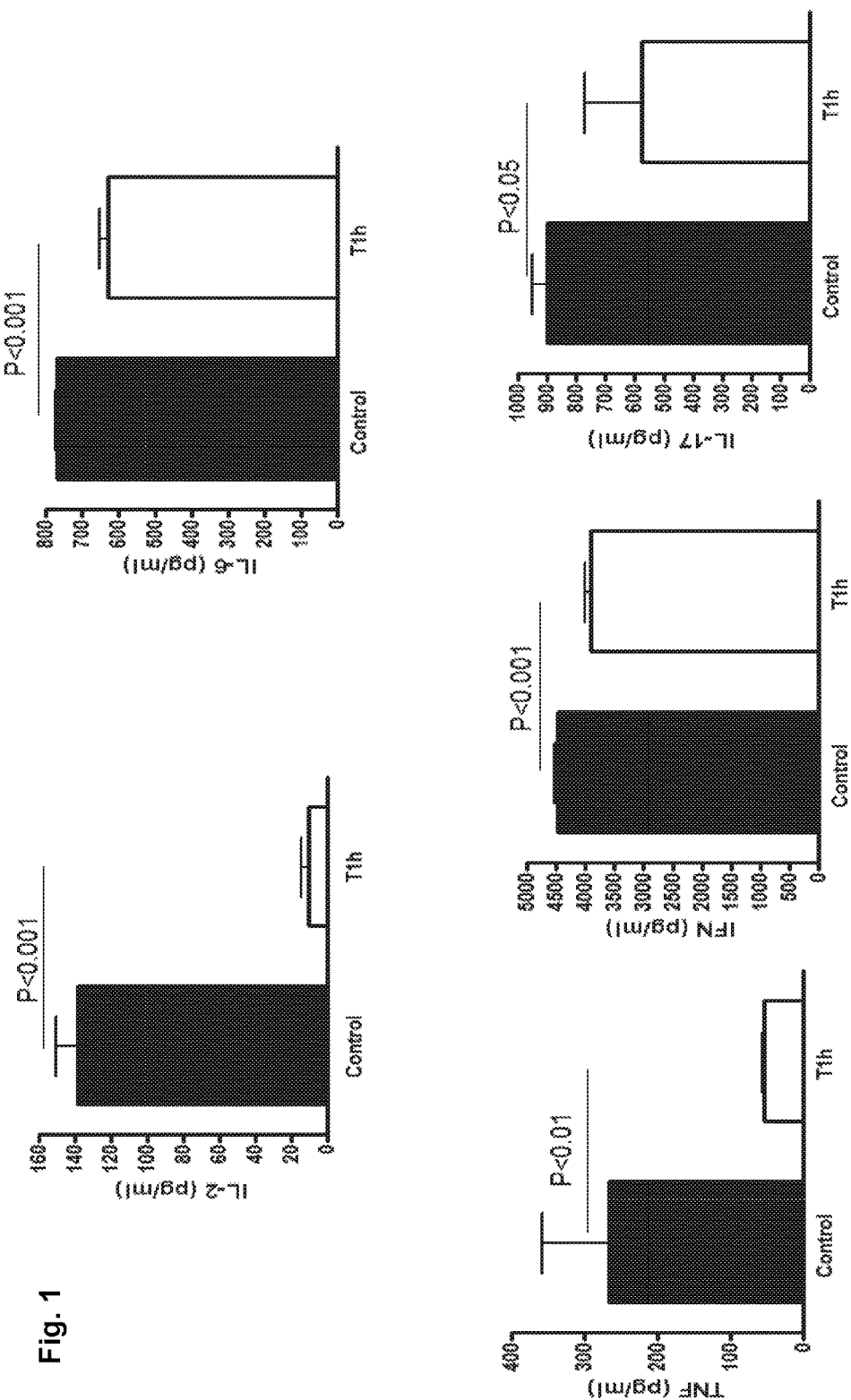

Petermann et al. (Immunity 33, 351-363 (2011)).*
Marwaha et al., Frontiers in Immunology, vol. 3, 2012, pp. 1-8.*
Schnyder et al., Cytokine 31 (2005) 191-202.*
Forrester et al., International Reviews of Immunology, 32:76-96, Feb. 2013.*
Dick et al., Ophthalmology Jan. 3, 2013;120:777-787.*
Barr et al. (J Exp Med. May 7, 2012;209(5):1001-10). (Year: 2012).*
Alonso-Ramirez, Ruby et al. "Rationale for Targeting CD6 as a Treatment for Autoimmune Diseases." 2010, *Arthritis*, 89:1-9.
Annunziato, Francesco. et al. "Phenotypic and functional features of human Th17 cells." 2007, *J Exp Med* 204(8): 1849-61.
Bettelli, Estelle et al. "Induction and effector functions of T(H)17 cells." 2008, *Nature* 453(7198): 1051-7.
Brucklacher-Waldert, Verena et al. "Phenotypical and functional characterization of T helper 17 cells in multiple sclerosis." 2009, *Brain* 132(Pt 12): 3329-41.
Croxford, Andrew L. et al. "IL-23 One cytokine in control of autoimmunity." 2012, *European Journal of Immunology*, 42:2263-2273.
De Wit, Jelle, et al. "CD5 costimulation induces stable Th17 development by promoting IL-23R expression and sustained STAT3 activation." 2011, *Blood* 118(23): 6107-14.
Gaffen, Sarah L. "Role of IL-17 in the Pathogenesis of Rheumatoid Arthritis." 2009, *Current Rheumatology Rep*. 11:5:365-370.
Kleinewietfeld, Marcus et al. CCR6 expression defines regulatory effector/memory—ke cells within the CD25(+)CD4+ T-cell subset.: 2005, *Blood* 105(7): 2877-86.
Liao, Fang et al. "CC-chemokine receptor 6 is expressed on diverse memory subsets of T cells and determines responsiveness to macrophage inflammatory protein 3 alpha." 1999, *J Immunol* 162(1): 186-94.
Liu, Hong et al. "Regulation of IL-17 in human $CCR6^+$ effector memory T cells." 2008, *J Immunol* 180(12): 7948-57.
Nair, P. et al. "CD6 synergistic co-stimulation promoting proinflammatory response is modulated without interfering with the activated leucocyte cell adhesion molecule interaction." 2010, *Clin Exp Immunol* 162(1): 116-30.
Pinto, Mafalda et al. "CD6 as a Therapeutic Target in Autoimmune Diseases: Successes and Challenges." 2013, *Biodrugs* 27:191-202.
Rodriguez, Pedro C. et al. "A clinical exploratory study with itolizumab, an anti-CD6 monoclonal antibody, in patients with rheumatoid arthritis." 2012, *Results in Immunology*, 2:2014-211.
Sallusto, Federica et al. "Flexible programs of chemokine receptor expression on human polarized T helper 1 and 2 lymphocytes." 1998, *J Exp Med* 187(6): 875-83.
Singh, Satya P. et al. "Human T cells that are able to produce IL-17 express the chemokine receptor CCR6." 2008, *Imunol* 180(1): 214-21.
Yamazaki, Tomohide, et al. "CCR6 regulates the migration of inflammatory and regulatory T cells." 2008, *J Immunol* 181(12): 8391-401.
"Biocon Receives Marketing Authorization for its Novel Biologic Itolizumab for Psoriasis." www.pharmachat.com/biocon-recieves-marketing-authorization-for-its-novel-biologic-itolizumab-for-psoriasis/, Jan. 8, 2013.
Le Dantec, Christelle et al. "Rationale for treating primary Sjögren's syndrome patients with an anti-CD6 monoclonal antibody (Itolizumab)." 2013, *Immunol Res*, 56:341-347.
Toussirot, Eric, "The IL23/Th17 Pathway as a Therapeutic Target in Chronic Inflammatory Diseases." 2012, *Inflammation & Allergy* 11:15-168.
Alonso, et al., "Towards the Definition of a Chimpanzee and Human Conversed CD6 Domain 1 Epitope Recognized by T1 Monoclonal Antibody." *Hybridoma* (2008); 27(4): 291-301.
Aranami, et al., "Th17 Cells and Autoimmune Encephalomyelitis (EAE/MS)." *Allergology International* (2008); 57 (2): 115-120.

Aruffo, Alejandro et al. "CD6-ligand interactions: a paradigm for SRCR domain function?" *Immunol. Today* (1997), vol. 18, No. 10, pp. 498-504.
Aulton, et al., Pharmaceutics: The Science of Dosage Form Design, 2nd Ed., pp. 276-288 (2001).
Browning, Jeffrey L. "B cells move to centre stage: novel opportunities for autoimmune disease treatment." *Nature Reviews Drug Discovery* (2006) vol. 5, pp. 564-576.
Cheifetz, Adam et al. "The Incidence and Management of Infusion Reactions to Infliximab: A Large Center Experience." The American Journal of Gastroenterology, (2003) vol. 98, No. 6, pp. 1315-1324.
Chen et al. "Inhibition of TFGβ1 by Anti-TFGβ1 Antibody or Lisinopril Reduces Thyroid Fibrosis m Granulomatous Experimental Autoimmune Thyroiditis." J Immunol. Dec. 1, 2002; 169(11):6530-6538.
Cleland, Jeffrey L. et al. A Specific Molar Ratio of Stabilizer to Protein is Required for Storage Stability of a Lyophilized Monoclonal Antibody. Journal of Pharmaceutical Sciences, Mar. 2001, vol. 90, No. 3, pp. 310-321.
Chopra, et al., "Itolizumab in combination with methotrexate modulates active rheumatoid arthritis: safety and efficacy from a phase 2, randomized, open-label, parallel-group, dose-arranging study." Clinical Rheumatology (2016); 35(4): 1059-1064. Epub Jun. 7, 2015.
Den Broeder, Alfons et al. "A Single Dose, Placebo Controlled Study of the Fully Human Anti-Tumor Necrosis Factor-a Antibody Adalimumab (D2E7) in Patients with Rheumatoid Arthritis." The Journal of Rheumatology (2002) vol. 29, No. 11, pp. 2288-2298.
Dillman, "Monoclonal antibodies for treating cancer." Annals of Internal Medicine (1989); 111: 592-603.
Edwards, Jonathan C.W. et al. "Efficacy of B-Cell-Targeted Therapy with Rituximab in Patients with Rheumatoid Arthritis." The New England Journal of Medicine (2004) vol. 350, pp. 2572-2581.
Extended European Search Report, corresponding to European Patent Application No. 10831248.9, dated Sep. 8, 2014.
Feldmann, Marc and et al. "Design of effective immunotherapy for humanautoimmunity." Nature (2005) vol. 435, pp. 612-619.
Fuss et al. "Nonclassical CD1d-restricted NK T cells that produce IL-13 characterize an atypical Th2 response in ulcerative colitis." The Journal of Clinical Investigation, vol. 113 No. 10, May 2004, p. 1490-1497.
Garber, Ken. "First-in-class biologic to enter rheumatoid arthritis fray." Nature (2005) vol. 23, No. 11, pp. 1323-1324.
Garcia, et al., ["Phase1 clinical trial of IOR-T1 monoclonal antibody in T lymphoma: pharmacokinetics and immune response."] Cuban Journal of Medicine, v. 42, No. 2, 2003, pp. 1-7, Google automated English language translation of Spanish original).
Garcia, et al., Cuban Journal of Medicine, v. 42, No. 2, 2003, pp. 1-7, Spanish language document.
Goldblatt, F. et al. "New therapies for rheumatoid arthritis." Clinical and Experimental Immunology (2005) vol. 140, pp. 195-204.
Goldsby, et al., Immunology, 2002, Freeman Press, pp. 290-291.
Hale, Douglas A., "Biological effects of induction immunosuppression." Current Opinion in Immunology (2004) vol. 16, pp. 565-570.
Harrison, P.V. et al., "Short-term methotrexate administration by low-dose-infusion does it influence clearance of psoriasis?" Clinical and Experimental Dermatology (1989) vol. 14, pp. 291-294.
Heldin et al. "Dimerization of Cell Surface Receptors in Signal Transduction." Cell. Jan. 27, 1995; 80(2):213-233.
Hernández, et al., "Therapeutic Targeting of CD6 in Autoimmune Diseases: A Review of Cuban Clinical Studies with the Antibodies IOR-T1 and Itolizumab." Current Drug Targets (2016); 17(6): 1-12.
Heydendael, Vera M.R. et al. "Methotrexate versus Cyclosporine in Moderate to-Severe Chronic Plaque Psoriasis." The New England Journal of Medicine (2003) vol. 349, pp. 658-665.
Horwitz et al. "Decreased Production of Interleukin-12 and Other Th1-Type Cytokines in Patients with Recent-Onset Systemic Lupus Erythematosus." Arthritis Rheum. May 1998;41(5): 838-844.
Ibáñez, et al., "Mitogen-Activated Protein Kinase Pathway Activation by the CD6 Lymphocyte Surface Receptor." Journal of Immunology, Jul. 2006, vol. 177(2): 1152-1159.
International Preliminary Report on Patentability for International Application No. PCT/IB2010/055296, dated May 20, 2012, 4 pages.

(56) References Cited

OTHER PUBLICATIONS

International Preliminary Report on Patentability for International Application No. PCT/IB2014/063345, dated Jan. 26, 2016, 7 pages.
International Preliminary Report on Patentability for International Application No. PCT/IN2008/000562, dated May 27, 2010, 10 pages.
International Preliminary Report on Patentability in International Application No. PCT/CU2007/000021, dated Oct. 6, 2009, and English translation, 24 pages.
International Preliminary Report on Patentability, and English translation, for International Application No. PCT/CU2007/000022, dated Oct. 6, 2009, 20 pages.
International Search Report and Written Opinion for International Application No. PCT/IB2010/055296, dated Mar. 4, 2011, 11 pages.
International Search Report and Written Opinion for International Application No. PCT/IB2014/063345, dated Nov. 18, 2014, 9 pages.
International Search Report and Written Opinion for International Application No. PCT/IN2008/000562, dated Mar. 4, 2009, 10 pages.
International Search Report for International Application No. PCT/CU2007/000022, dated Apr. 28, 2008, 4 pages.
International Search Report Written Opinion in International Application No. PCT/CU2007/000021, dated Apr. 21, 2008, and English translation, 22 pages.
Jadidi-Niaragh and Mirshafiey, "Th17 Cell, the New Player of Neuroinflammatory Process in Multiple Sclerosis." Scandinavian Journal of Immunology (2011); 74(1): 1-13.
Joo, et al. "Evidence for the Expression of a Second CD6 Ligand by Synovial Fibroblasts." Arthritis and Rheumatism (2000) vol. 43, No. 2, pp. 329-335.
Kahan, Barry D. "Individuality: the barrier to optimal immunosuppression."Nature Reviews Immunology (2003) vol. 3, pp. 831-838.
Krauss, et al., "Impact of antibody framework residue VH-71 on the stability of a humanised anti-MUC1 scFv and derived immunoenzyme." British Journal of Cancer (2004); 90: 1863-1870.
Kremer, Joel M. et al. "Treatment of Rheumatoid Arthritis with the Selective Costimulation Modulator Abatacept." Arthritis & Rheumatism (2005) vol. 52, No. 8, pp. 2263-2271.
Larrick, J.W. and Gavilondo, J., "Meeting Report: Therapeutic antibody technology 97." Immunotechnology. Jan. 1998, vol. 3, pp. 303-307.
Mavilia et al. "Type 2 Helper T-Cell Predominance and High CD30 Expression in Systemic Sclerosis." Am J. Pathol. Dec. 1997;151(6): 1751-1758.
Mease, Philip. "Infliximab (Remicade) in the treatment of psoriatic arthritis."Therapeutic and Clinical Risk Management, 2006: 2(4), pp. 389-400.
Montero, E. et al. "Immunodiagnosis and therapeutic immunosuppression in rheumatoid arthritis with ior t1 (anti-CD6) monoclonal antibody." Arthritis Research, vol. 4, No. Suppl. 1, 2002, abstract 114, 1 page. Autoimmunity (1999); 29(2): 155-156.
Montero, et al. "Immunodiagnosis and therapeutic immunosuppression in rheumatoid arthritis ior t1 (anti-CD6) monoclonal antibody." Abstracts of the 22nd European Workshop for Rheumatology Research, Arthritis Research (2002), 4 (suppl 1) Meeting Abstract #114, one page.
Nair, et al., "The inhibition of T cell proliferation in a mixed lymphocyte reaction by Itolizumab (T1h) is associated with reduction in pro inflammatory cytokines and CD6 internalization. (52. 27)" The Journal of Immunology (2011); 186 (1 Supplement) (Meeting Abstract Supplement); http://www.jimmunol.org/content/186/1_Supplement/52.27.short.
O'Dell, James R. "Therapeutic Strategies for Rheumatoid Arthritis." The New England Journal of Medicine (2004) vol. 350, pp. 2591-2602.
Olsen, Nancy J. et al. "New Drugs for Rheumatoid Arthritis." The New England Journal of Medicine (2004) vol. 350, pp. 2167-2179.
Osorio, et al., "CD6 ligation modulates the Bcl-2/Bax ratio and protects chronic lymphocytic leukemia B cells from apoptosis induced by anti-IgM." Blood (1997); 89(8): 2833-2841.
Patel, D.D. "CD6" Journal of Biological Regulators and Homeostatic Agents (2000) vol. 14, No. 3, pp. 234-236.
Pincus, T. et al. "Methotrexate as the "anchor drug" for the treatment of early rheumatoid arthritis." Clin Exp Rheumatol (2003) vol. 21 (Suppl 31) pp. S179-S185.
Pincus, Theodore et al. "Combination Therapy with Multiple Disease-Modifying Antirheumatic Drugs in Rheumatoid Arthritis: A Preventative Strategy." Ann Intern Med (1999) vol. 131, No. 10, pp. 768-774.
Reddy, Manjula P. et al. "Elimination of F c Receptor-Dependent Effector Functions of a Modified IgG4 Monoclonal Antibody to Human CD4." The Journal of Immunology (2000) vol. 164, pp. 1925-1933.
Roep et al. "Satisfaction (not) guaranteed: re-evaluating the use of animal models of type 1 diabetes." Nat Rev Immunol. Dec. 2004; 4(12): 989-997.
Roep, Bart. "Are Insights Gained from NOD Mice Sufficient to Guide Clinical Translation? Another Inconvenient Truth." Ann. N.Y. Acad. Sci. (2007); 1103: 1-10.
Roque-Navarro et al., "Humanization of Predicted T-Cell Epitopes Reduces the Immunogenicity of Chimeric Antibodies: New Evidence Supporting a Simple Method," Hybridoma and Hybridomics (2003), 22(4): 245-257.
Rostami, et al., "Role of Th17 cells in the pathogenesis of CNS inflammatory demyelination." Journal of Neurological Sciences (2013); 333 (1-2): 76-87.
Sanguine BioScience, "Types of immune cells present in human PBMC," Nov. 2012, 5 pages.
Singer, N.G. et al., "CD6: expression during development, apoptosis and selection of human and mouse thymocytes." International Immunology, Jun. 2002, vol. 14 No. 6, pp. 585-597.
Smolen, Josef S. et al. "Therapeutic Strategies for Rheumatoid Arthritis." Nature Reviews Drug Discovery (2003) vol. 2, pp. 473-488.
Starling, Gary C. et al. "Characterization of mouse CD6 with novel monoclonal antibodies which enhance the allogeneic mixed leukocyte reaction." Eur. J. Immunol. 1996. 26:738-746.
Stohl and Looney, "B cell depletion therapy in systemic rheumatic diseases: Different strokes for different folks?" Clinical Immunology (2006), vol. 121. pp. 1-12.
Strober, Bruce E. et al. "Folate supplementation during methotrexate therapy for patients with psoriasis." Journal of American Dermatology (2005) vol. 53, No. 4, pp. 652-659.
Strom and Suthanthiran, "Therapeutic Approach to Organ Translation. Therapeutic Immunology" edited by Austen et al., Blackwell Science, Cambridge, MA, 1996; pp. 451-456.
Summons to attend Oral Proceedings, corresponding to European Patent Application No. 08873217.7, dated Feb. 6, 2015, 9 pages.
Swierkot, Jerzy et al. "Methotrexate in rheumatoid arthritis." Pharmacological Reports (2006) vol. 58, pp. 473-492.
Taylor, Peter C. et al. "New approaches to therapeutic immunomodulation for immune-mediated inflammatory disorders." Current Opinion (2004); vol. 4, pp. 368-371.
The Biocon press release of Jun. 22, 2004, one page, http://www.biocon.com/biocon_press_archives_details.asp?subLink=news&Fileid=91, downloaded Feb. 15, 2013.
The Biocon press release of Nov. 30, 2006, one page, http://www.biocon.com/biocon_press_release_details.asp?subLink=news&Fileid=235, downloaded Feb. 15, 2013.
Written Opinion, and English translation, for International Application No. PCT/CU2007/000022, dated Apr. 28, 2008, 18 pages.
Youdim, Adrienne et al. "A Pilot Study of Adalimumab in Infliximab-Allergic Patients." Inflamm Bowel Dis (2004) vol. 10, No. 4 pp. 333-338.
Zimmerman, Aukje W. et al. "Long-term engagement of CD6 and ALCAM is essential for T-cell proliferation induced by dendritic cells." Blood (2006); 107(8): 3212-3220.

* cited by examiner

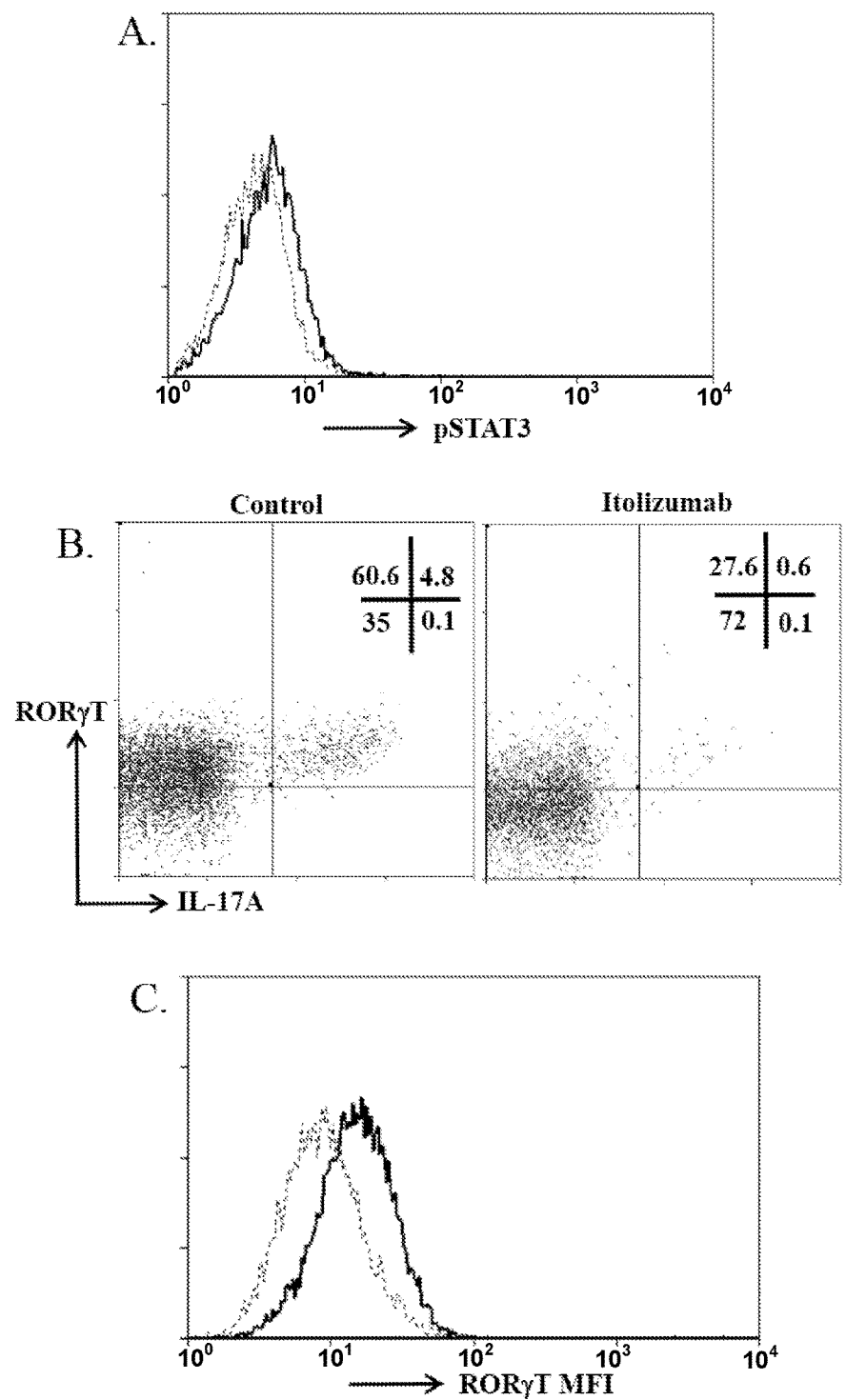
Fig. 6 (continued on next page)

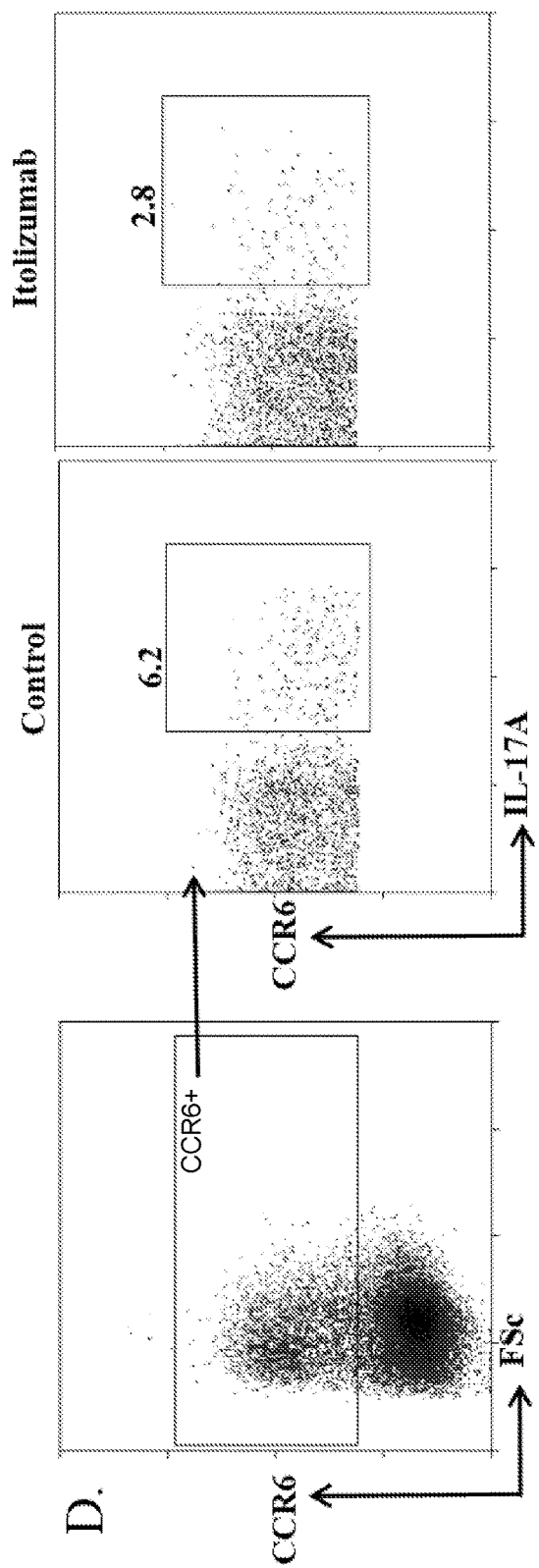
Fig. 6 (continued from previous page)

USE OF A CD6 BINDING PARTNER AND METHOD BASED THEREON

CROSS-REFERENCE TO RELATED APPLICATIONS

This application is filed under the provisions of 35 U.S.C. § 371 and claims the priority of International Patent Application No. PCT/IB2004/063345 filed on Jul. 23, 2014, which in turn claims the benefit of and the priority to provisional Indian patent application 3264/CHE/2013 filed on 23 Jul. 2013 with the Indian Patent Office. The content of said application filed on 23 Jul. 2013 is incorporated herein by reference for all purposes in its entirety, including an incorporation of any element or part of the description, claims or drawings not contained herein and referred to in Rule 20.5(a) of the PCT, pursuant to Rule 4.18 of the PCT.

TECHNICAL FIELD

The present disclosure relates to a method and a use of a CD6 binding partner. In particular, the present disclosure relates to a method for treatment, including prevention, of disease conditions mediated by T-helper 17 (Th17) and/or T-helper 1 (Th1) T lymphocytes (T cells). Furthermore, the present disclosure relates to the use of anti-CD6 binding partner for treatment of disease conditions mediated by auto-reactive Th17 and Th1 T lymphocytes. The binding partners, compositions, methods and uses of the present disclosure further have utility in methods and uses for modulating an immune response by suppressing the production of the cytokine IL-23R (interleukin 23 receptor), thereby decreasing inflammation mediated by Th17 cells.

BACKGROUND OF THE DISCLOSURE

The following discussion of the background of the disclosure is merely provided to aid the reader in understanding the binding partners, compositions, methods and uses described in this document, and is not admitted to describe or constitute prior art.

Protective immunity against certain diseases is dependent on the differential induction of specific pro-inflammatory T-cell (T lymphocyte) populations by antigen presenting cells (APCs) of the innate immune system, such as dendritic cells (DCs) and macrophages. Two such T-cell populations, responsible for mediating cellular immunity to a wide range of pathogens, are Th1 and Th17 cells. Both Th1 and more recently Th17 T cell populations have been implicated as mediators of autoimmune and chronic inflammatory diseases, and thus serve as relevant cellular targets for immunosuppressive agents. Furthermore, Dendritic Cells, as initiators of T-cell responses, are a second cellular target for therapies designed to combat inflammatory disease. Multiple Sclerosis (MS) is an inflammatory autoimmune disorder of the central nervous system (CNS), characterized by inflammatory infiltrates of T-cells, B cells, macrophages and focal demyelinating plaques within the CNS. Both Th1 and Th17 cell-mediated responses have been shown to play a role in the development of inflammatory demyelination. Myelin-reactive T-cells from MS patients produce cytokines consistent with a Th1-mediated response, while microarray studies of MS lesions from patients demonstrate increased expression of IL-23R.

A relevant model for studying the mechanisms of autoimmune inflammatory responses, and in particular MS, is the experimental autoimmune encephalomyelitis (EAE) animal model of inflammatory demyelinating disease that shares clinical and neuropathological changes with multiple sclerosis (MS). It has been accepted for many years that EAE is largely a CD4+Th1-mediated disease, though a pathogenic role for CD8+ T-cells in the induction of EAE has also been demonstrated. More recently however, it has been demonstrated that an IL-17 producing T cell subset plays a critical role in the pathogenesis of EAE. While there is still some debate in the literature, it is likely that Th1 and Th17 cells cooperate to induce the development of organ-specific autoimmunity.

CD6 is an important cell surface protein predominantly expressed by human T cells and a subset of B cells, as well as by some B cell chronic lymphocytic leukemias and neurons [Aruffo et al., J. Exp. Med. 1991, 174:949; Kantoun et al., J. Immunol. 1981, 127:987; Mayer et al., J. Neuroimmunol. 1990. 29:193]. CD6 is a member of a large family of proteins characterized by having at least one domain homologous to the scavenger receptor cysteine-rich domain (SRCR) of type I macrophages [Matsumoto, et al., J. Exp. Med. 1991, 173:55 and Resnick et al., Trends Biochem. Sci. 1994, 19:5]. Other members of this family include CD5 [Jones et al., Nature. 1986, 323:346]; cyclophilin C [Friedman et al. 1993, PNAS 90:6815]; complement factor I, which binds activated complement proteins C3b and C4b [Goldberger, et al., J. Biol. Chem. 1987, 262:10065]; bovine WC-1 expressed by .tau./.delta. T cells [Wijingaard et al., J. Immunol. 1992, 149:3273] and M130 [Law et al., Eur J. Immunol. 1993, 23:2320], a macrophage activation marker.

Blocking studies using anti-CD6 monoclonal antibodies (mAbs) suggest that CD6 plays an important role in T cell development by regulating T cell adhesive interactions with thymic epithelial (TE) cells (Patel et al., J. Exp. Med. (1995) 181:1563-1568). Additional studies have shown that CD6 can function as an important accessory molecule in T cell activation. For example, certain anti-CD6 mAb are directly mitogenic for T cells (Gangemi et al., J. Immunol. (1989) 143:2439; Bott et al., Int. Immunol. (1993) 7:783), whereas others are able to co-stimulate T cell proliferation in conjunction with anti-CD3, anti-CD2 or PMA (Gangemi et al., J. Immunol. (1989) 143:2439; Morimoto et al., J. Immunol. (1988) 140:2165-2170; Osorio et al., Cell. Immunol. (1994) 154:23). Yet additional evidence of the role of CD6 in T cell activation comes from studies showing that CD6 becomes hyperphosphorylated on Ser and Thr residues (Swack et al., Mol. Immunol. (1989) 26:1037-1049; Swack et al., J. Biol. Chem. (1991) 266:7137; Cardenas et al., J. Immunol., 145:1450-1455 (1990)) and phosphorylated on Tyr residues (Wee et al., J. Exp. Med. (1993) 177:219-223) following T cell activation. These and other studies implicate CD6 as an important modulator of both immature and mature T cell function in vivo, affecting both T cell activation and signal transduction (De Wit, J., et al., Blood (2011) 118:6107-6114).

BRIEF DESCRIPTION OF THE ACCOMPANYING FIGURES

In order that the disclosure may be readily understood and put into practical effect, reference will now be made to exemplary embodiments as illustrated with reference to the accompanying Figures. The Figures together with the detailed description below, are incorporated in and form part of the specification, and serve to further illustrate the embodiments and explain various principles and advantages, in accordance with the present disclosure:

FIG. 1 depicts inhibition of Th1 and Th17 cytokines by the humanized monoclonal antibody Itolizumab as compared to an isotype control antibody, namely the humanized monoclonal antibody Nimotuzumab ("T1h"), in a mixed lymphocyte reaction assay.

Figure 2:
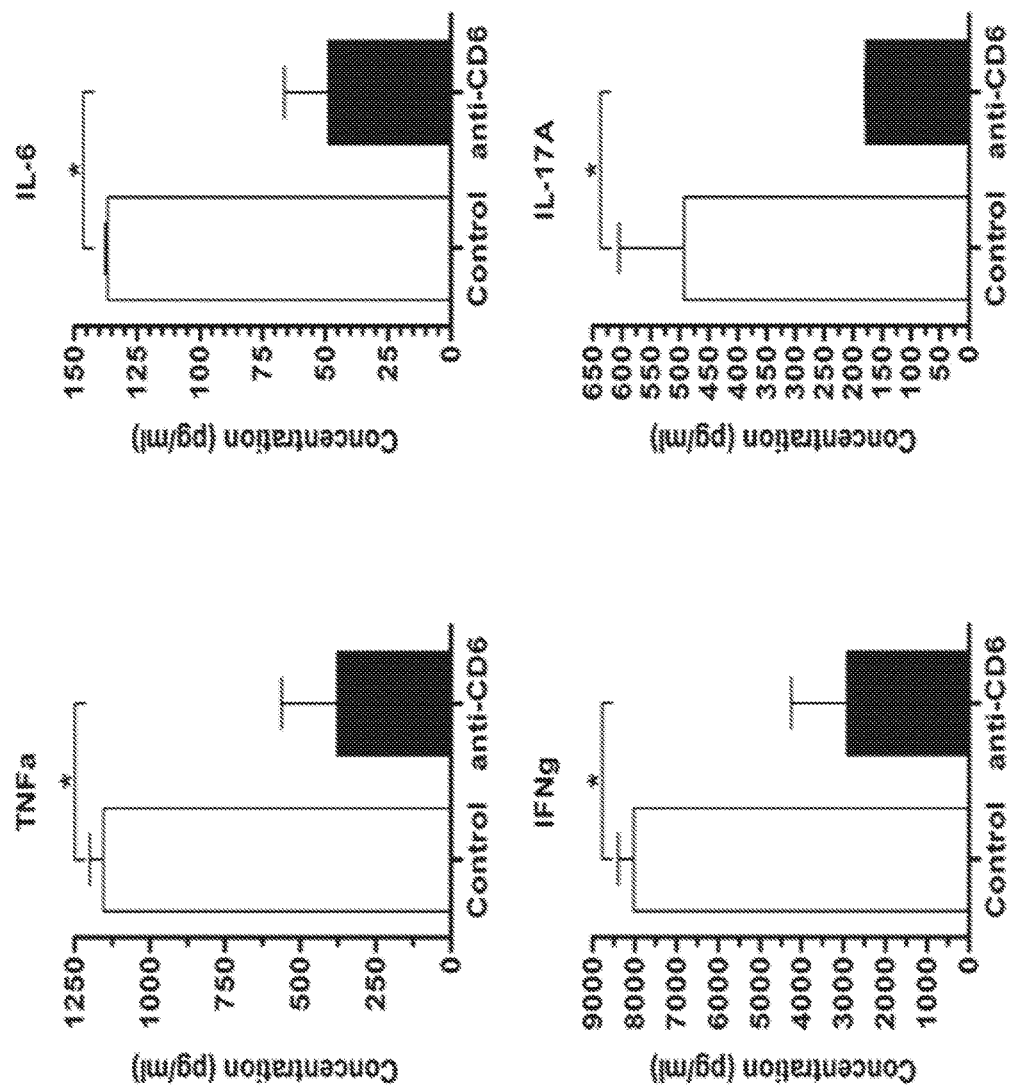

FIG. 2: An anti-mouse CD6 domain 1 specific antibody (surrogate antibody to Itolizumab) shows the inhibition of Th1 and Th17 cytokines. Splenocytes from EAE induced animals treated with anti-mouse CD6 antibody, and a group treated with rat antibody were re-stimulated in culture with an anti CD3 antibody. The group treated with the rat antibody showed high proliferation with associated release of high amounts of Th1 and Th17 cytokines. On the other hand, the anti-mouse CD6 treated group of animals showed decreased proliferation and lower release of Th1 and Th17 specific cytokines in this mouse model of MS.

Figure 3:
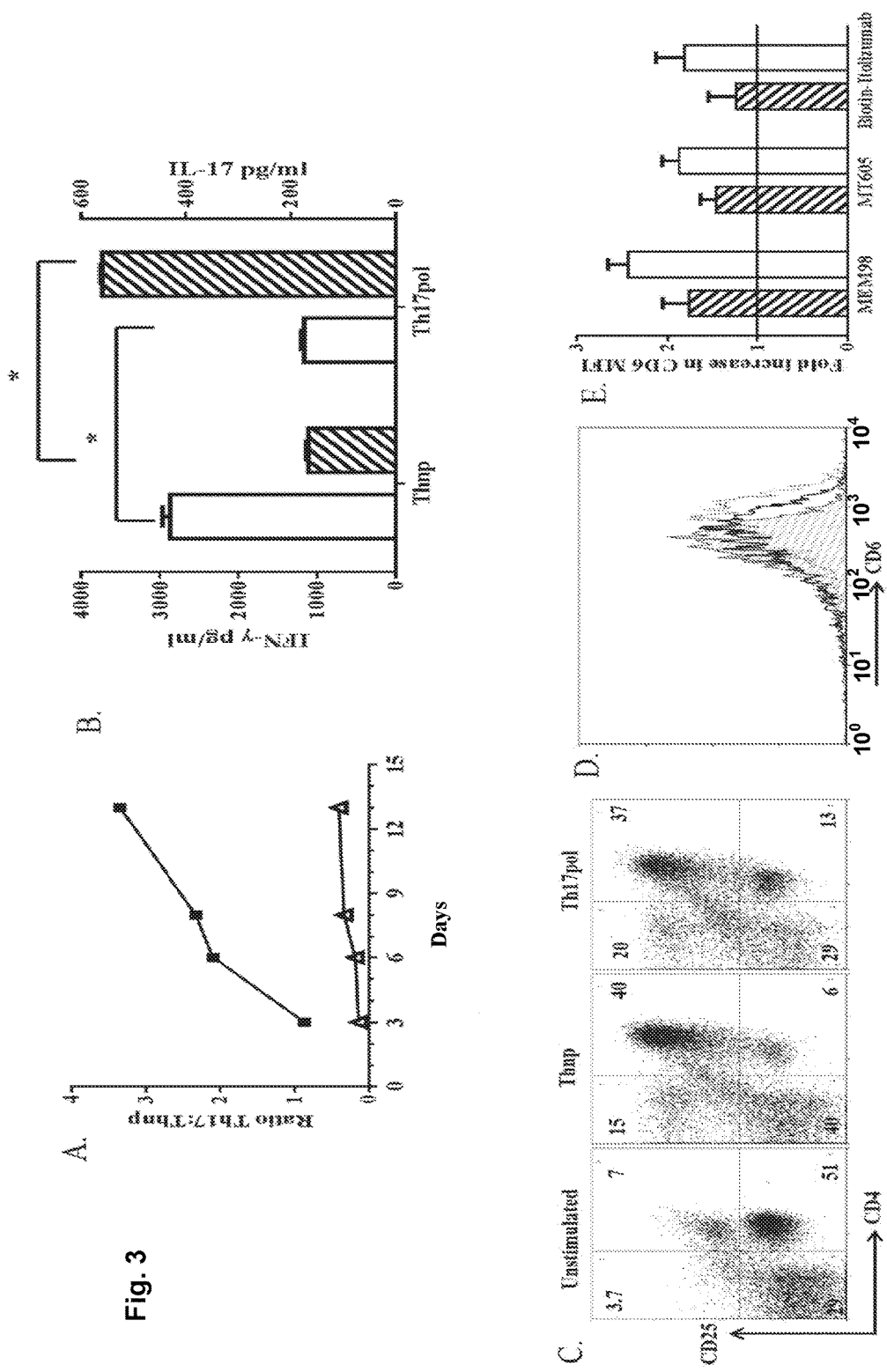

FIG. 3: CD6 overexpression in pro-inflammatory $CD4^+T$ cell subsets:

(A) PBMCs were stimulated in Thnp (nonpolarizing for CD4+ T cells) or Th17pol (Th17-polarizing) conditions, supernatant was collected from quadruplicate wells, pooled and analyzed using ELISA for secreted IFN-γ (Th1 signature cytokine) and IL-17 (Th17 signature cytokine). Ratio of absolute concentration of IFN-γ (empty triangle) or IL-17A (filled square) in Th17pol and Thnp conditions (Th17pol: Thnp) is plotted across the days of analysis. (B) Absolute levels of IFN-γ (empty bars) and IL-17 (shaded bars) on day 13 is compared between Thnp and Th17pol conditions. Data shown is mean±SD for triplicate ELISA wells (p<0.001) (C) PBMCs were left unstimulated or stimulated in Thnp or Th17pol conditions. CD25 expression on $CD4^+T$ cells was analyzed on Day 3. (D) PBMCs were left unstimulated (shaded histogram) or stimulated in Thnp (solid line) or Th17pol (dotted line) conditions. CD6 expression (using biotin Itolizumab as detection reagent) was analyzed on Day 9 and plotted as CD6 overlay histograms gated on $CD4^+T$ cells. (E) Fold increase in CD6 MFI on gated $CD4^+T$ cells was calculated over unstimulated, and plotted as bar graph for both Thnp (shaded bar) and Th17pol (empty bar) conditions using 3 different antibodies as CD6 detection reagent i.e. MEM98, MT605 and Biotinylated Itolizumab. Data shown is mean±SD (p<0.05). In panel A-C, data are representative of 2 independent experiments from different donors and in panel D&E data are representative of 2 independent experiments from 6 different donors.

Figure 4:
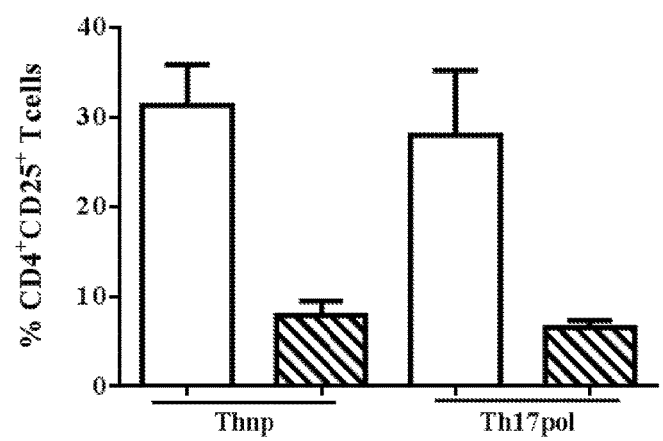
Figure 4:
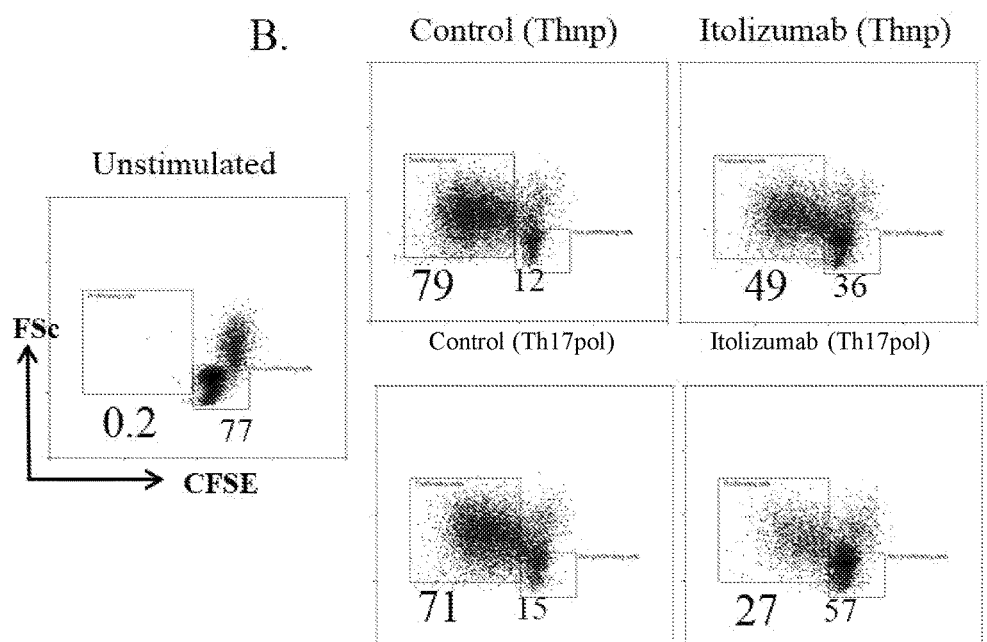

FIG. 4: Itolizumab Inhibits T cell activation and proliferation in both Thnp and Th17pol conditions:

(A) PBMCs were stimulated in Thnp or Th17pol conditions in presence of Itolizumab or control antibody. On day 3 cells were analyzed for CD25 expression on gated $CD4^+T$ cells. % $CD4^+CD25^+T$ cells in stimulated PBMCs, is plotted as bar graphs. Data shown is mean±SD from 2 independent experiments from different donors. (B) PBMCs labelled with CFSE dye were stimulated in Thnp or Th17pol conditions in presence of Itolizumab or control antibody. On day 3 cells were analyzed for CFSE dilution on gated $CD4^+T$ cells. Data shown is from 1 experiment.

Figure 5:
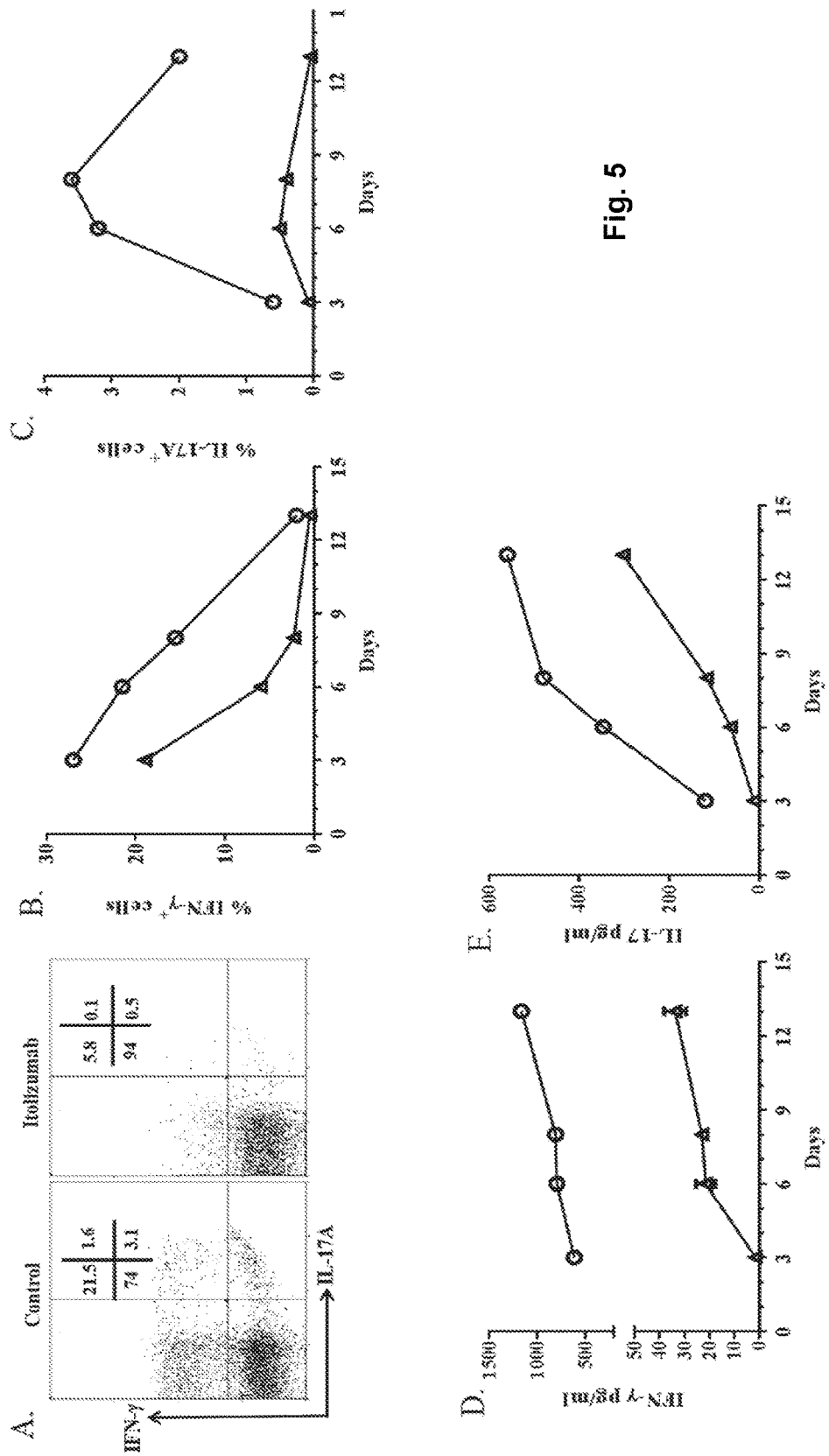

FIG. 5: Itolizumab treatment causes substantial reduction in expression of IL-17 and IFN-γ cytokines in cells stimulated in Th17 polarizing condition:

PBMCs were stimulated in Th17pol conditions in presence of Itolizumab or control antibody. On days 3, 6, 8 and 13, cells stimulated in Th17pol conditions with control or Itolizumab monoclonal antibody, were restimulated with PMA-Ionomycin for 5 hours and analyzed for expression of intracellular cytokine IFN-γ and IL-17A. Representative flow cytometry dot plots (on gated $CD3^+T$ cells) on day 6 are shown in panel A. Panel B & C show the % of IFN-$γ^+T$ cells and IL-17$A^+T$ cells respectively, in presence of Itolizumab (empty triangle) or control antibody (empty circle), across days as obtained from flow cytometry analysis. Data is representative of 2 independent experiments from different donors. To analyze the basal level of secreted cytokines, supernatants were collected from quadruplicate wells of PBMCs stimulated in Th17pol conditions in presence of Itolizumab (empty triangle) or control antibody (empty circle). As evaluated by ELISA, secreted (D) IFN-γ and (E) IL-17 levels are plotted across days. In Panel D and E data is shown as mean+SD (p<0.0001) and representative of 2 independent experiments from different donors.

FIG. 6: Itolizumab causes reduction in signature Th17 specific markers:

(A) PBMCs were stimulated in Th17pol conditions in presence of control or Itolizumab antibody and analyzed on Day 3 for expression of transcription factor pSTAT3. Data shown is histogram for pSTAT3 on gated $CD4^+T$ cells. (B) Cells stimulated in Th17pol conditions in presence of control or Itolizumab antibody were restimulated with PMA-Ionomycin for 5 hours and analyzed for expression of intracellular cytokine IL-17A and Th17 signature transcription factor RORγT. Day 6 representative dot plots of RORγT and IL-17A on gated $CD3^+T$ cells are shown. (C) Data from panel B was plotted as histogram overlays of RORγT MFI on gated $CD3^+T$ cells stimulated in Th17pol conditions in presence of control (empty histogram) or Itolizumab (dotted line histogram) antibodies. Data shown is representative of 2 independent similar experiments from different donors. (D) For the experiment as explained in panel A, Day 6 representative dot plots of CCR6 and IL-17A on gated $CD3^+CCR6^+T$ cells are shown.

SUMMARY OF THE DISCLOSURE

Disclosed herein are methods, uses and compositions directed at treating, including preventing, an autoimmune disease in a subject, as well as treating, including preventing, allograft rejection, and treating, including preventing, graft-versus-host disease. A respective method and use includes administering to the subject a therapeutically effective amount of a binding partner specifically binding to CD6.

The present disclosure relates to methods for treatment, including prevention, of disease conditions mediated by T-helper 17 (Th17) and/or T-helper 1 (Th1) T lymphocytes (T cells). In particular, the present disclosure relates to the use of an anti-CD6 antibody for the treatment of disease conditions mediated by auto-reactive Th17 and Th1 T lymphocytes. The methods of the disclosure further have utility in methods for modulating an immune response by suppressing the production of the cytokine IL-23R, thereby decreasing inflammation mediated by Th17 cells.

In a first aspect there is provided a method of treating a subject suffering from (i) an autoimmune disease characterized by an increased number of T helper 17 (Th17) T lymphocytes, (ii) allograft rejection, or (iii) graft-versus-host disease. Thus the subject is known or suspected to have an increased number of T helper 17 (Th17) T lymphocytes when compared to a healthy subject. The method includes administering to the subject a binding partner specifically binding to CD6.

In a second aspect there is provided a binding partner specifically binding to CD6 for use in the treatment of (i) an autoimmune disease, (ii) allograft rejection, or (iii) graft-versus-host disease in a subject. The subject is known or suspected to have an increased number of T helper 17

(Th17) T lymphocytes when compared to a healthy subject. These Th17 T lymphocytes may be auto-reactive Th17 T lymphocytes.

In some embodiments of the method according to the first aspect or of the binding partner specifically binding to CD6 for use according to the second aspect the subject is furthermore known or suspected to have an increased number of T helper 1 (Th1) cells when compared to a healthy subject. These Th1 T lymphocytes may be auto-reactive Th1 T lymphocytes.

In some embodiments of the method according to the first aspect or of the binding partner specifically binding to CD6 for use according to the second aspect the subject the autoimmune disease is rheumatoid arthritis. In some embodiments the autoimmune disease is Inflammatory Bowel Disease. The autoimmune disease may for example be Crohn's disease. In some embodiments the autoimmune disease is ulcerative colitis. The autoimmune disease is in some embodiments psoriasis. In some embodiments the autoimmune disease is Sjögren's syndrome. In some embodiments the autoimmune disease is Ankylosing spondylitis. In some embodiments the autoimmune disease is Type I diabetes.

In some embodiments of the method according to the first aspect or of the binding partner specifically binding to CD6 for use according to the second aspect the subject the binding partner is an antibody such as an immunoglobulin. The antibody may for example be a polyclonal immunoglobulin. In some embodiments the antibody is a monoclonal antibody. In some embodiments the antibody is a fully non-human antibody. In some embodiments the antibody is a chimeric antibody. The antibody is in some embodiments a humanized antibody. In some embodiments the antibody is a fully human antibody such as a fully human immunoglobulin. An illustrative example of a humanized antibody is Itolizumab.

In some embodiments of the method according to the first aspect or of the binding partner specifically binding to CD6 for use according to the second aspect the subject the binding partner is a functional fragment of an immunoglobulin. In some embodiments a respective functional immunoglobulin fragment is a Fab-fragment. In some embodiments the functional immunoglobulin fragment is a single-chain variable fragment (scFv). In some embodiments the functional immunoglobulin fragment is a nanobody.

In some embodiments the binding partner specifically binding to CD6 is included in a pharmaceutical composition. The pharmaceutical composition includes the binding partner specifically binding to CD6 and at least one pharmaceutically acceptable diluent, carrier or excipient.

In a third aspect there is provided a method of treating a subject suffering from (i) an autoimmune disease characterized by an increased number of T helper 17 (Th17) T lymphocytes, (ii) allograft rejection, or (iii) graft-versus-host disease. Thus the subject is known or suspected to have an increased number of T helper 17 (Th17) T lymphocytes when compared to a healthy subject. The method includes administering to the subject a binding partner specifically binding to CD6 and a binding partner specifically binding to CD3. In some embodiments the binding partner specifically binding to CD6 and the binding partner specifically binding to CD3 are administered independent from one another. In some embodiments the binding partner specifically binding to CD6 and the binding partner specifically binding to CD3 are administered concomitantly.

In a fourth aspect there is provided a combination of a binding partner specifically binding to CD6 and a binding partner specifically binding to CD3 for use in the treatment of (i) an autoimmune disease, (ii) allograft rejection, or (iii) graft-versus-host disease in a subject. The subject is known or suspected to have an increased number of T helper 17 (Th17) T lymphocytes when compared to a healthy subject. These Th17 T lymphocytes may be auto-reactive Th17 T lymphocytes.

In a fifth aspect there is provided a pharmaceutical composition for the treatment of an autoimmune disease in a subject known or suspected to have an increased number of Th17 cells when compared to a healthy subject. The pharmaceutical composition includes a binding partner specifically binding to CD6 and at least one pharmaceutically acceptable diluent, carrier or excipient.

In a sixth aspect there is provided a pharmaceutical composition for the treatment of an autoimmune disease in a subject known or suspected to have an increased number of Th17 cells when compared to a healthy subject. The pharmaceutical composition includes a binding partner specifically binding to CD6. The pharmaceutical composition also includes a binding partner specifically binding to CD3. Furthermore the pharmaceutical composition includes at least one pharmaceutically acceptable diluent, carrier or excipient.

DETAILED DESCRIPTION OF THE DISCLOSURE

Definitions

Unless otherwise stated, the following terms used in this document, including the description and claims, have the definitions given below.

The word "about" as used herein refers to a value being within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. The term "about" is also used to indicate that the amount or value in question may be the value designated or some other value that is approximately the same. The phrase is intended to convey that similar values promote equivalent results or effects according to the binding partners, compositions, methods and uses described herein. In this context "about" may refer to a range above and/or below of up to 10%. The word "about" refers in some embodiments to a range above and below a certain value that is up to 5%, such as up to up to 2%, up to 1%, or up to 0.5% above or below that value. In one embodiment "about" refers to a range up to 0.1% above and below a given value.

The term "administering", as used herein, refers to any mode of transferring, delivering, introducing, or transporting matter such as a compound, e.g. a pharmaceutical compound, or other agent such as an antigen, to a subject. Modes of administration include oral administration, topical contact, intravenous, intraperitoneal, intramuscular, intranasal, or subcutaneous administration (cf. below). Administration "in combination with" further matter such as one or more therapeutic agents includes simultaneous (concurrent) and consecutive administration in any order.

The term "antibody" generally refers to an immunoglobulin, a fragment thereof or a proteinaceous binding molecule with immunoglobulin-like functions (cf. below).

The term "binding partner" as used herein refers to matter, such as a molecule, in particular a polymeric molecule, that can bind a nucleic acid molecule such as a DNA or an RNA molecule, including an mRNA molecule, as well as a peptide, a protein, a saccharide, a polysaccharide or a lipid through an interaction that is sufficient to permit the agent to form a complex with the nucleic acid molecule, peptide, protein or saccharide, a polysaccharide or a lipid, generally via non-covalent bonding. In some embodiments the binding partner is a PNA molecule. In some embodiments the binding partner is an immunoglobulin or a proteinaceous binding molecule with immunoglobulin-like functions as defined below. In some embodiments the binding partner is an aptamer. In some embodiments a binding partner is specific for a particular target. In some embodiments a binding partner includes a plurality of binding sites, each binding site being specific for a particular target. As an illustrative example, a binding partner may be a proteinaceous agent with immunoglobulin-like functions with two binding sites. It may for instance be a bispecific diabody, such as a bispecific single chain diabody.

As used herein, the term "chimeric antibody" refers to an immunoglobulin polypeptide or domain antibody that includes sequences from more than one species. In a chimeric antibody a heavy chain or a light chain may contain a variable region sequence from one species such as human and a constant region sequence from another species such as mouse. As an example, a "chimeric antibody" may be an immunoglobulin that has variable regions derived from an animal antibody, such as a rat or mouse antibody, fused to another molecule, for example, the constant domains derived from a human antibody. The term "chimeric antibody" is intended to encompass antibodies in which: (i) the heavy chain is chimeric but the light chain comprises V and C regions from only one species; (ii) the light chain is chimeric but the heavy chain comprises V and C regions from only one species; and (iii) both the heavy chain and the light chain are chimeric.

In this regard, a "humanized antibody" as used herein is an immunoglobulin polypeptide or domain antibody containing structural elements of a human antibody and the antigen binding site of a non-human antibody. "Humanized antibodies" contain a minimal number of residues from the non-human antibody. For instance, they may contain only the CDR regions of the non-human antibody, or only those residues that make up the hypervariable regions of the non-human antibody. They may also contain certain residues from outside the variable regions of the non-human polypeptide, such as residues that are necessary to mimic the structure of the non-human antibody or to minimize steric interference. Typically a humanized antibody contains a human framework, at least one CDR from a non-human antibody, with any constant region present being substantially identical to a human immunoglobulin constant region, i.e., at least about 85-90%, such as at least 95% identical. Hence, all parts of a humanized immunoglobulin, except possibly the CDRs, are substantially identical to corresponding parts of one or more native human immunoglobulin sequences. In addition, humanized antibodies may contain residues that do not correspond to either the human or the non-human antibodies.

The term "detect" or "detecting", as well as the term "determine" or "determining" when used in the context of a biomarker, refers to any method that can be used to detect the presence of a nucleic acid (DNA and RNA) or a protein/polypeptide. When used herein in combination with the words "level", "amount" or "value", the words "detect", "detecting", "determine" or "determining" are understood to generally refer to a quantitative or a qualitative level.

Accordingly, a method or use as disclosed herein may include a quantification of Th17 cells in absolute numbers. A method or use as disclosed herein may also include a comparison by measuring a relative amount of Th17 cells, for example compared to a reference sample from one or more healthy subjects. As a further example, absolute amounts of IL-17A or TNFα may in some embodiments be measured. In some embodiments it may be analysed whether a first sample contains a higher or a lower or the same amount of IL-17A or TNFα than a second sample. The terms "value," "amount" and "level" also refer to the rate of synthesis of for example IL-17A, TNFα, IL-22, IL-17F, IL-21, or IL-6. The exact nature of the "level", "amount" or "value" depends on the specific design and components of the particular analytical method employed to detect T cells or e.g. IL-17A, TNFα, IL-22, IL-17F, IL-21, or IL-6.

An "effective amount" or a "therapeutically effective amount" of an agent such as a binding partner, is an amount—either as a single dose or as part of a series of doses—sufficient to provide a therapeutic benefit in the treatment or management of the relevant pathological condition, or to delay or minimize one or more symptoms associated with the presence of the condition. Such a condition may be associated with immunosuppression, e.g. an autoimmune disease.

The terms "expressing" and "expression" in reference to a biomarker are intended to be understood in the ordinary meaning as used in the art. A biomarker is expressed by a cell via transcription of a nucleic acid into mRNA, followed by translation into a polypeptide, which is folded and possibly further processed. The biomarkers discussed in this disclosure are in addition being transported to the surface of the respective cell. Hence, the statement that a cell is expressing such a biomarker indicates that the biomarker is found on the surface of the cell and implies that the biomarker has been synthesized by the expression machinery of the respective cell. Accordingly, the term "expression level" in the context of a cell population such as T cells refers to the number or percentage of cells that have the biomarker of interest on their cell surface. The determination of expression may be based on the normalized expression level of the biomarkers. Expression levels are normalized by correcting the absolute expression level of a biomarker by comparing its expression to the expression of a gene that is not a biomarker in the context of the invention. The expression level may also be provided as a relative expression level.

With regard to the respective biological process itself, the terms "expression", "gene expression" or "expressing" refer to the entirety of regulatory pathways converting the information encoded in the nucleic acid sequence of a gene first into messenger RNA (mRNA) and then to a protein. Accordingly, the expression of a gene includes its transcription into a primary hnRNA, the processing of this hnRNA into a mature RNA and the translation of the mRNA sequence into the corresponding amino acid sequence of the protein. In this context, it is also noted that the term "gene product" refers not only to a protein, including e.g. a final protein (including a splice variant thereof) encoded by that gene and a respective precursor protein where applicable, but also to the respective mRNA, which may be regarded as the "first gene product" during the course of gene expression.

By "fragment" in reference to a polypeptide such as an immunoglobulin or a proteinaceous binding molecule is meant any amino acid sequence present in a corresponding polypeptide, as long as it is shorter than the full length sequence and as long as it is capable of performing the function of interest of the protein—in the case of an immunoglobulin specifically binding to the desired target, e.g. antigen (CD6, for example). The term "immunoglobulin fragment" refers to a portion of an immunoglobulin, often the hypervariable region and portions of the surrounding heavy and light chains that displays specific binding affinity for a particular molecule. A hypervariable region is a portion of an immunoglobulin that physically binds to the polypeptide target. Due to the usage in the art, the terms "antibody fragment" and "immunoglobulin fragment" are used interchangeably herein.

A "functional fragment" as used herein, refers to a fragment of a molecule such as a peptide or a nucleic acid molecule, which retains at least one biological activity of the full length molecule. In the context of an immunoglobulin a functional fragment is an immunologically functional fragment. Typically a functional fragment of a peptide is capable of performing substantially the same functions as those of the intact polypeptide.

As used in this document, the expression "pharmaceutically acceptable" refers to those active compounds, materials, compositions, carriers, and/or dosage forms which are, within the scope of sound medical judgment, suitable for use in contact with the tissues of human beings and animals without excessive toxicity, irritation, allergic response, or other problems or complications, commensurate with a reasonable benefit/risk ratio.

The terms "polypeptide" and "protein" refer to a polymer of amino acid residues and are not limited to a certain minimum length of the product. Where both terms are used concurrently, this twofold naming accounts for the use of both terms side by side in the art.

The term "preventing" in the medical/physiological context, i.e. in the context of a physiological state, refers to decreasing the probability that an organism contracts or develops an abnormal condition.

The term "specific" as used in this document is understood to indicate that a binding partner is directed against, binds to, or reacts with a biomarker disclosed in the present application, such as CD6. Thus, being directed to, binding to or reacting with includes that the binding partner specifically binds to e.g. CD6. The term "specifically" in this context means that the binding partner reacts with CD6, as applicable, or/and a portion thereof, but at least essentially not with another protein. The term "another protein" includes any protein, including proteins closely related to or being homologous to e.g. CD6 against which the binding partner is directed to. The term "does not essentially bind" means that the binding partner does not have particular affinity to another protein, i.e., shows a cross-reactivity of less than about 30%, when compared to the affinity to CD6. In some embodiments the binding partner shows a cross-reactivity of less than about 20%, such as less than about 10%. In some embodiments the binding partner shows a cross-reactivity of less than about 9, 8, or 7%, when compared to the affinity to CD6. In some embodiments the binding partner shows a cross-reactivity of less than about 6%, such as less than about 5%, when compared to the affinity to e.g. CD6. Whether the binding partner specifically reacts as defined herein above can easily be tested, inter alia, by comparing the reaction of a respective binding partner with e.g. CD6, as applicable, and the reaction of the binding partner with (an) other protein(s). The term "specifically recognizing", which can be used interchangeably with the terms "directed to" or "reacting with" means in the context of the present disclosure that a particular molecule, generally an immunoglobulin, an immunoglobulin fragment or a proteinaceous binding molecule with immunoglobulin-like functions is capable of specifically interacting with and/or binding to at least two, including at least three, such as at least four or even more amino acids of an epitope as defined herein. Generally the immunoglobulin or proteinaceous binding molecule can thereby form a complex with the respective epitope of e.g. CD6. Such binding may be exemplified by the specificity of a "lock-and-key-principle". "Specific binding" can also be determined, for example, in accordance with a Western blot, ELISA-, RIA-, ECL-, IRMA-test, FACS, IHC and a peptide scan.

The term "Surrogate antibody" as used herein is understood to indicate the surrogate antibody to Itolizumab that was developed in-house to study the effects of an Anti CD6 domain 1 binding antibody in mice and is identified as a rat anti mouse CD6 IgG 2c. It has the equivalent properties to Itolizumab as 1. Binds to domain 1 of mouse CD6, 2. Does not compete with ALCAM binding. 3. Inhibits the proliferation of naïve T cells from splenocytes stimulated with anti CD3. 4. Is not systemically depleting in mice. 5. Has a comparable affinity to that of T1h.

The term "subject" as used herein, also addressed as an individual, refers to a human or non-human animal, generally a mammal. A subject may be a mammalian species such as a rabbit, a mouse, a rat, a Guinea pig, a hamster, a dog, a cat, a pig, a cow, a goat, a sheep, a horse, a monkey, an ape or a human. Thus, the methods, uses and compositions described in this document are applicable to both human and veterinary disease. The sample has been obtained from the subject. Where the same is a body fluid sample or a biopsy sample, it may be obtained using conventional techniques routinely employed in the art. It is thus understood that conclusions drawn from expression levels in the sample and decisions based thereon concern the subject from whom/which the sample has been taken. Where the subject is a living human who is receiving medical care for a disease or condition, it is also addressed as a "patient".

The terms "treatment" and "treating" as used herein, refer to a prophylactic or preventative measure having a therapeutic effect and preventing, slowing down (lessen), or at least partially alleviating or abrogating an abnormal, including pathologic, condition in the organism of a subject. Those in need of treatment include those already with the disorder as well as those prone to having the disorder or those in whom the disorder is to be prevented (prophylaxis). Generally a treatment reduces, stabilizes, or inhibits progression of a symptom that is associated with the presence and/or progression of a disease or pathological condition. The term "administering" relates to a method of incorporating a compound into cells or tissues of a subject. The term "therapeutic effect" refers to the inhibition or activation of factors causing or contributing to the abnormal condition. A therapeutic effect relieves to some extent one or more of the symptoms of an abnormal condition or disease. The term "abnormal condition" refers to a function in the cells or tissues of an organism that deviates from their normal functions in that organism. An abnormal condition can inter alia relate to cell proliferation, cell differentiation, or cell survival.

The terms "comprising", "including," containing", "having" etc. shall be read expansively or open-ended and without limitation. Singular forms such as "a", "an" or "the" include plural references unless the context clearly indicates otherwise. Thus, for example, reference to a "vector" includes a single vector as well as a plurality of vectors, either the same—e.g. the same operon—or different. Likewise reference to "cell" includes a single cell as well as a plurality of cells. Unless otherwise indicated, the term "at least" preceding a series of elements is to be understood to refer to every element in the series. The terms "at least one" and "at least one of" include for example, one, two, three, four, or five or more elements. It is furthermore understood that slight variations above and below a stated range can be used to achieve substantially the same results as a value within the range. Also, unless indicated otherwise, the disclosure of ranges is intended as a continuous range including every value between the minimum and maximum values.

The scope and meaning of any use of a term will be apparent from the specific context in which the term is used. Certain further definitions for selected terms used throughout this document are given in the appropriate context of the detailed description, as applicable. Unless otherwise defined, all other scientific and technical terms used in the description, figures and claims have their ordinary meaning as commonly understood by one of ordinary skill in the art.

Methods and Uses for Treating a Disease

The present inventors made the surprising finding that anti CD6 antibody mediated co-stimulation with an anti-CD3 antibody is of high significance, and apparently more significant as compared to the co-stimulation induced by anti CD28/CD3, which primes naive T cells for stable Th17 development by promoting the expression of IL-23R. Thus, the anti-CD6 antibody has immunosuppressive activity and acts to selectively suppress Th1 and Th17 (IL-23R producing T cell) mediated inflammatory autoimmune disease.

Without wishing to be bound by theory, the inventors predict that IL-23R is expressed by antigen presenting cells, such as dendritic cells and macrophages. The expression of IL-23R by the antigen presenting cells skews the resulting T cell response away from the expansion of T cells with a Th1 and Th17 phenotype which can in some instances become auto-reactive T cells which mediate autoimmune and chronic inflammatory conditions.

The current therapies for the treatment of autoimmune and chronic inflammatory diseases, such as multiple sclerosis, are mainly focused on the use of steroids and other NSAIDs, which are non-specific and have serious side effects. In particular, certain such treatments primarily act to suppress the expression or functional activity of Tumor necrosis factor alpha (TNF-alpha). For example, the chimeric monoclonal antibody INFLIXIMAB (Remicade®) targets TNF-alpha function. Although effective in certain patients, such anti-TNF-alpha treatments can be ineffective when treating certain patients, or certain autoimmune conditions, or further, could also result in the occurrence of undesirable side effects.

The inventors have identified the utility of a binding partner or composition of the present disclosure in the treatment of Th1 and/or Th 17-mediated diseases and conditions, in particular autoimmune or immune-mediated conditions, which occur where aberrant Th1 and/or Th17 responses occur due to the occurrence of auto-reactive Th1 and/or Th17 T cells.

A subject to be treated according to the present disclosure is known or suspected to have an increased number of Th17 T cells when compared to a healthy subject. Th17 T cells were named after their production of the signature cytokine IL-17A. In addition Th17 T cells also produce IL-17F, IL-21, IL-22, GM-CSF, TNFα and IL-6.

The presence of an increased number of Th17 T cells in a subject may be detected by analyzing the T cells present in body fluid in a subject or body fluid obtained from a subject.

The presence of an increased number of Th17 T cells in a subject may be detected by analyzing the level of cytokines known to be produced by Th17 T cells. Accordingly in some embodiments an increased number of Th17 T cells in a subject may be detected by detecting the level of IL-17A in the subject and comparing the level to the level of IL-17A in a healthy subject. In some embodiments an increased number of Th17 T cells in a subject may be detected by detecting the level of TNFα in the subject and comparing the level to the level of TNFα in a healthy subject. In some embodiments an increased number of Th17 T cells in a subject may be detected by detecting the level of IL-6 in the subject and comparing the level to the level of TNFα in a healthy subject. In some embodiments an increased number of Th17 T cells in a subject may be detected by detecting the level of Interferon gamma (IFN-γ) in the subject and comparing the level to the level of Interferon gamma in a healthy subject.

A binding partner disclosed herein specifically binds to CD6. "CD6" is an abbreviation of "Cluster of Differentiation 6". The protein is also called T-cell differentiation antigen CD6, as well as T12 or TP120. CD6 is in some embodiments the mouse protein of SwissProt/UniProt accession no. Q61003 (version 117 of 9 Jul. 2014). In some embodiments CD6 is the human protein with the SwissProt/UniProt accession no. P30203 (version 125 of 9 Jul. 2014). In some embodiments CD6 is isoform d of the human protein CD6, having SwissProt/UniProt accession no. Q8WWJ4 (version 59 of 16 Apr. 2014). In some embodiments CD6 is isoform c of the human protein CD6, having SwissProt/UniProt accession no. Q8WWJ6 (version 59 of 16 Apr. 2014). In some embodiments CD6 is isoform b of the human protein CD6, having SwissProt/UniProt accession no. Q8WWJ3 (version 59 of 16 Apr. 2014). In some embodiments CD6 is isoform e of the human protein CD6, having SwissProt/UniProt accession no. Q8WWJ7 (version 60 of 16 Apr. 2014). In some embodiments CD6 is the human protein of SwissProt/UniProt accession no. Q8N4Q7 (version 66 of 16 Apr. 2014). In some embodiments CD6 is isoform CRA_d of the human protein CD6, having SwissProt/UniProt accession no. G5E973 (version 26 of 9 Jul. 2014). In some embodiments CD6 is the rat protein with the SwissProt/UniProt accession no. Q5FVU4 (version 69 of 9 Jul. 2014). In some embodiments CD6 is the Rhesus macaque (*Macaca mulatta*) protein with the SwissProt/UniProt accession no. H9ZFC2 (version 7 of 16 Apr. 2014).

In some embodiments of a method or use disclosed herein, IL-23R expression on blood cells and/or dendritic cells of the subject is being analysed. In some embodiments the level of one or more of TNF-alpha, IFN-gamma, IL-17, and IL-17A in a body fluid of the patient is being analysed. In a mixed lymphocyte reaction, it is observed that the Th1 and Th17 cytokine IL17A is reduced in presence of T1h as illustrated in FIG. 1. In animal models using surrogate antibody to domain 1 of CD6, reduction in Th1 and Th17 (IL17A) cytokines is observed as illustrated in FIG. 2.

Any available method can be used to detect the presence of a nucleic acid or a protein in the context of the present invention. Such a method may include established standard procedures well known in the art. Examples of such techniques include, but are not limited to, RT-PCR, RNAse protection assay, Northern analysis, Western analysis, ELISA, radioimmunoassay or fluorescence titration assay. Assessing the amount of a biomarker such as IL-17, IFN-gamma or TNF-alpha in/on a cell may include assessing the amount of a nucleic acid, e.g. RNA, in a cell encoding the respective biomarker. A nucleic acid probe may be used to probe a sample by any common hybridization method to detect the amount of nucleic acid molecules of the biomarker. In order to obtain nucleic acid probes chemical synthesis can be carried out. The synthesized nucleic acid probes may be first used as primers in a polymerase chain reaction (PCR) carried out in accordance with recognized PCR techniques, essentially according to standard PCR protocols utilizing the appropriate template, in order to obtain the respective probe. One skilled in the art will readily be able to design such a probe based on the sequences available for the biomarker. The hybridization probe can be labeled by standard labeling techniques such as with a radiolabel, enzyme label, fluorescent label, biotin-avidin label, chemiluminescence or a nanoparticle. After hybridization, the probes may be visualized using a standard technique.

A detection method used in the context of the present invention may include an amplification of the signal caused by the nucleic acid or protein, such as a polymerase chain reaction (PCR) or the use of the biotin-streptavidin system, for example in form of a conjugation to an immunoglobulin, as also explained in more detail below. The detection method may for example include the use of an antibody, e.g. an immunoglobulin, which may be linked to an attached label, such as for instance in Western analysis or ELISA. Where desired, an intracellular immunoglobulin may be used for detection. Some or all of the steps of detection may be part of an automated detection system. Illustrative examples of such systems are automated real-time PCR platforms, automated nucleic acid isolation platforms, PCR product analysers and real-time detection systems. As indicated above, the term "antibody" as used herein, is understood to include an immunoglobulin and an immunoglobulin fragment that is capable of specifically binding a selected protein, e.g. L-selectin or a protein specific for T cells, as well as a respective proteinaceous binding molecule with immunoglobulin-like functions. An antibody may for instance be an EGF-like domain, a Kringle-domain, a fibronectin type I domain, a fibronectin type II domain, a fibronectin type III domain, a PAN domain, a Gla domain, a SRCR domain, a Kunitz/Bovine pancreatic trypsin Inhibitor domain, tendamistat, a Kazal-type serine protease inhibitor domain, a Trefoil (P-type) domain, a von Willebrand factor type C domain, an Anaphylatoxin-like domain, a CUB domain, a thyroglobulin type I repeat, an LDL-receptor class A domain, a Sushi domain, a Link domain, a Thrombospondin type I domain, an immunoglobulin domain or a an immunoglobulin-like domain (for example a domain antibody or a camel heavy chain antibody), a C-type lectin domain, a MAM domain, a von Willebrand factor type A domain, a Somatomedin B domain, a WAP-type four disulfide core domain, a F5/8 type C domain, a Hemopexin domain, an SH2 domain, an SH3 domain, a Laminin-type EGF-like domain, a C2 domain, a "Kappabody" (Ill. et al., Protein Eng (1997) 10, 949-957), a "Minibody" (Martin et al., EMBO J (1994) 13, 5303-5309), a "Diabody" (Holliger et al., PNAS U.S.A. 90, 6444-6448 (1993)), a "Janusin" (Traunecker et al., EMBO J (1991) 10, 3655-3659 or Traunecker et al., Int J Cancer (1992) Suppl 7, 51-52), a nanobody, an adnectin, a tetranectin, a microbody, an affilin, an affibody or an ankyrin, a crystallin, a knottin, ubiquitin, a zinc-finger protein, an autofluorescent protein, an ankyrin or ankyrin repeat protein or a leucine-rich repeat protein (cf. also below).

A measurement of a level or amount may for instance rely on spectroscopic, photochemical, photometric, fluorometric, radiological, enzymatic or thermodynamic means. An example of a spectroscopical detection method is fluorescence correlation spectroscopy. A photochemical method is for instance photochemical cross-linking. The use of photoactive, fluorescent, radioactive or enzymatic labels respectively are examples for photometric, fluorometric, radiological and enzymatic detection methods. An example of a thermodynamic detection method is isothermal titration calorimetry. As an illustrative example of a label, a detailed protocol on the use of water-soluble, bio-functionalized semiconductor quantum dots has been given by Lidke et al. (Current Protocols in Cell Biology, [2007] Suppl. 36, 25.1.1-25.1.18). Such quantum dots have a particularly high photostability, allowing monitoring their localization for minutes to hours to days. They are typically fluorescent nanoparticles. Since different types of quantum dots can be excited by a single laser line multi-colour labelling can be performed. Detection can for example conveniently be carried out in different fluorescence channels of a flow cytometer. A quantum dot can be coupled to a binding partner of IL-17, IFN-gamma or TNF-alpha.

The measurement used is generally selected to be of a sensitivity that allows detection of the cells expressing the biomarker of interest, e.g IL-17, IFN-gamma or TNF-alpha, in the range of a selected threshold value, in particular of a sensitivity that allows determining whether IL-17, IFN-gamma or TNF-alpha expressing cells are below the threshold value. Typically a binding partner of IL-17, IFN-gamma or TNF-alpha, respectively, may be used in combination with a detectable marker. Such a binding partner of IL-17, IFN-gamma or TNF-alpha has a detectable affinity and specificity for IL-17, IFN-gamma or TNF-alpha, respectively. Typically, binding is considered specific when the binding affinity is higher than 10-6 M. A binding partner of e.g. IL-17, IFN-gamma, TNF-alpha, or IL-23R, respectively, has in some embodiments an affinity of about $10^{-8}$ M or higher, or of about $10^{-9}$ M or higher.

A respective binding partner of e.g. IL-17, IFN-gamma, TNF-alpha, or IL-23R, as well as a binding partner for another selected cell-characteristic protein, may be an immunoglobulin, a fragment thereof or a proteinaceous binding molecule with immunoglobulin-like functions. An antibody fragment generally contains an antigen binding or variable region. Examples of (recombinant) antibody fragments are immunoglobulin fragments such as Fab fragments, Fab' fragments, Fv fragments, single-chain Fv fragments (scFv), diabodies or domain antibodies (Holt, L. J., et al., Trends Biotechnol. (2003), 21, 11, 484-490). An example of a proteinaceous binding molecule with immunoglobulin-like functions is a mutein based on a polypeptide of the lipocalin family (WO 03/029462, Beste et al., Proc. Natl. Acad. Sci. USA (1999) 96, 1898-1903). Lipocalins, such as the bilin binding protein, the human neutrophil gelatinase-associated lipocalin, human Apolipoprotein D or glycodelin, posses natural ligand-binding sites that can be modified so that they bind to selected small protein regions known as haptens. Examples of other proteinaceous binding molecules are the so-called glubodies (see e.g. international patent application WO 96/23879 or Napolitano, E. W., et al., Chemistry & Biology (1996) 3, 5, 359-367), proteins based on the ankyrin scaffold (Mosavi, L. K., et al., Protein Science (2004) 13, 6, 1435-1448) or crystalline scaffold (e.g. internation patent application WO 01/04144), the proteins described in Skerra, J. Mol. Recognit. (2000) 13, 167-187, AdNectins, tetranectins and avimers. Avimers contain so called A-domains that occur as strings of multiple domains in several cell surface receptors (Silverman, J., et al., Nature Biotechnology (2005) 23, 1556-1561). Adnectins, derived from a domain of human fibronectin, contain three loops that can be engineered for immunoglobulin-like binding to targets (Gill, D. S. & Damle, N. K., Current Opinion in Biotechnology (2006) 17, 653-658). Tetranectins, derived from the respective human homotrimeric protein, likewise contain loop regions in a C-type lectin domain that can be engineered for desired binding (ibid.). Peptoids, which can act as protein ligands, are oligo(N-alkyl) glycines that differ from peptides in that the side chain is connected to the amide nitrogen rather than the α carbon atom. Peptoids are typically resistant to proteases and other modifying enzymes and can have a much higher cell permeability than peptides (see e.g. Kwon, Y.-U., and Kodadek, T., J. Am. Chem. Soc. (2007) 129, 1508-1509). A suitable antibody may in some embodiments also be a multispecific antibody that includes several immunoglobulin fragments.

An immunoglobulin or a proteinaceous binding molecule with immunoglobulin-like functions may be PEGylated or hyperglycosylated if desired. In some embodiments a proteinaceous binding molecule with immunoglobulin-like functions is a fusion protein of one of the exemplary proteinaceous binding molecules above and an albumin-binding domain, for instance an albumin-binding domain of streptococcal protein G. In some embodiments a proteinaceous binding molecule with immunoglobulin-like functions is a fusion protein of an immunoglobulin fragment, such as a single-chain diabody, and an immunoglobulin binding domain, for instance a bacterial immunoglobulin binding domain. As an illustrative example, a single-chain diabody may be fused to domain B of staphylococcal protein A as described by Unverdorben et al. (Protein Engineering, Design & Selection [2012] 25, 81-88).

According to one aspect of the present disclosure, there is provided a method of treating or preventing an autoimmune disease which is caused by auto-reactive Th1 and/or Th17 T cells, the method including the steps of:
  providing a therapeutically effective amount of a composition including anti-CD6 antibody; and
  administering said antibody to a subject in need of such treatment in an amount sufficient to suppress the activation of T-helper 17 lymphocytes (Th17 T cells) and/or a T-helper 1 lymphocytes (Th1 T cells).

In some embodiments determining the level of expression of the gene of interest includes determining the level of transcription into mRNA. RNA encoding the protein of interest in the sample, such as IL-17, IFN-gamma, TNF-alpha, or IL-23R may be amplified using any available amplification technique, such as polymerase chain reaction (PCR), including multiplex PCR, nested PCR and amplification refractory mutation specific (ARMS) PCR (also called allele-specific PCR (AS-PCR), rolling circle amplification (RCA), nucleic acid sequence based amplification (NASBA), ligase chain reaction (LCR), QB replicase chain reaction, loop-mediated isothermal amplification (LAMP), transcription mediated amplification (TMA) and strand displacement amplification (SDA), including genome strand displacement amplification (WGSDA), multiple strand displacement amplification (MSDA), and gene specific strand displacement amplification (GS-MSDA). Detection of the obtained amplification products may be performed in numerous ways known in the art. Examples include, but are not limited to, electrophoretic methods such as agarose gel electrophoresis in combination with a staining such as ethidium bromide staining. In other embodiments the method of the invention is accompanied by real time detection, such as real time PCR. In these embodiments the time course of the amplification process is monitored. A means of real time detection commonly used in the art involves the addition of a dye before the amplification process. An example of such a dye is the fluorescence dye SYBR Green, which emits a fluorescence signal only when bound to double-stranded nucleic acids.

Typically a detectable label or marker is used. Such a marker or label may be included in a nucleic acid that includes the sequence to be amplified. A marker may also be included in a primer or a probe. It may also be incorporated into the amplification product in the course of the reaction. In some embodiments such a marker compound, e.g. included in a nucleic acid, is an optically detectable label, a fluorophore, or a chromophore. An illustrative example of a marker compound is 6-carboxyfluorescein (FAM).

As an illustrative example, real-time PCR may be used to determine the level of RNA encoding the protein of interest in the sample, such as IL-17, IFN-gamma, TNF-alpha, or IL-23R. Such a PCR procedure is carried out under real time detection, so that the time course of the amplification process is monitored. PCR is characterized by a logarithmic amplification of the target sequences. For the amplification of RNA, a reverse transcriptase-PCR is used. Design of the primers and probes required to detect expression of a biomarker of the invention is within the skill of a practitioner of ordinary skill in the art. In some embodiments RNA from the sample is isolated under RNAse free conditions and then converted to DNA via the use of a reverse transcriptase. Reverse transcription may be performed prior to RT-PCR analysis or simultaneously, within a single reaction vessel. RT-PCR probes are oligonucleotides that have a fluorescent moiety, also called reporter dye, attached to the 5' end and a quencher moiety coupled to the 3' end (or vice versa). These probes are typically designed to hybridize to an internal region of a PCR product. In the non-hybridized state, the proximity of the fluor and the quench molecules prevents the detection of fluorescent signal from the probe. During PCR amplification, when the polymerase replicates a template on which an RT-PCR probe is bound, the 5'-3' nuclease activity of the polymerase cleaves the probe. Thereby the fluorescent and quenching moieties are decoupled.

Fluorescence increases then in each cycle, in a manner proportional to the amount of probe cleavage. Fluorescence signal emitted from the reaction can be measured or followed over time using equipment which is commercially available using routine and conventional techniques. Quantitation of biomarker RNA in a sample being evaluated may be performed by comparison of the amplification signal to that of one or more standard curves where known quantities of RNA were evaluated in a similar manner. In some embodiments, the difference in biomarker expression is measured as the difference in PCR cycle time to reach a threshold fluorescence, or "dCT."

In some embodiments of a method or use disclosed herein an autoimmune disease is being treated. In certain embodiments of the present disclosure, the composition disclosed herein suppresses both a T-helper 17 lymphocyte (Th17) mediated immune response and a T-helper 1 lymphocyte (Th1) mediated immune response. In certain embodiments, the disease which is mediated by the auto-reactive T cells is an autoimmune disease or chronic inflammatory disease.

In certain embodiments of the present disclosure, the autoimmune disease is Multiple Sclerosis (MS). In some embodiments the autoimmune disease is Rheumatoid Arthritis (RA). In some embodiments the autoimmune disease is Inflammatory Bowel Disease (IBD) such as Crohn's disease. The autoimmune disease may in some embodiments be Ulcerative Colitis. In some embodiments the autoimmune disease is Type 1 Diabetes. In some embodiments the autoimmune disease is Psoriasis.

The listing or discussion of a previously published document in this specification should not necessarily be taken as an acknowledgement that the document is part of the state of the art or is common general knowledge.

The binding partners, compositions, methods and uses illustratively described herein may suitably be practiced in the absence of any element or elements, limitation or limitations, not specifically disclosed herein. Additionally, the terms and expressions employed herein have been used as terms of description and not of limitation, and there is no intention in the use of such terms and expressions of excluding any equivalents of the features shown and described or portions thereof, but it is recognized that various modifications are possible. Thus, it should be understood that although the present binding partners, compositions, methods and uses has been specifically disclosed by exemplary embodiments and optional features, modification and variation of the binding partners, compositions, methods and uses embodied therein herein disclosed may be resorted to by those skilled in the art, and that such modifications and variations are considered to be within the scope of the binding partners, compositions, methods and uses disclosed.

The binding partners, compositions, methods and uses have been described broadly and generically herein. Each of the narrower species and subgeneric groupings falling within the generic disclosure also form part of the binding partners, compositions, methods and uses. This includes the generic description of the binding partners, compositions, methods and uses with a proviso or negative limitation removing any subject matter from the genus, regardless of whether or not the excised material is specifically recited herein.

Other embodiments are within the appending claims. In addition, where features or aspects of the binding partners, compositions, methods and uses are described in terms of Markush groups, those skilled in the art will recognize that the binding partners, compositions, methods and uses is also thereby described in terms of any individual member or subgroup of members of the Markush group.

In order that the binding partners, compositions, methods and uses may be readily understood and put into practical effect, particular embodiments will now be described by way of the following non-limiting examples.

Example 1

Mixed Lymphocyte Reaction and Cytokine Analysis:
Preparation of PBMCs:
30 ml of blood is collected from a healthy donor. PBMCs are isolated by standard FICOLL density gradient centrifugation Monocyte Depletion & Setting up Dendritic Cell Derivation Assay: These cells are incubated in a CO2 incubator for two hours. Monocytes are allowed to adhere onto the plastic surface. The non-adhered cells (PBLs) are subsequently removed from the flasks. All the flasks are washed with 1×PBS once. 20 ml of DC media (made 50 ml stock, 10 µl of GMCSF and 5 µl of IL-4 in 50 ml of assay media) is added to each flask. The flasks are kept in CO2 incubator for 6 days.

LPS Treatment to On-Growing Dendritic Cells:
At day 6, DC media with LPS is added to each flask (final concentration of LPS in the flask is 4 ug/ml) and kept back in CO2 incubator for 40-48 hrs.

Preparation of Cells for Mixed Lymphocyte Assay:
Preparation of DCs:
After LPS treatment the cell suspension (DC) are collected from the two flasks. Each flask is washed with 1×PBS once. The cell suspension is spun down @ 1500 rpm for 5 minutes and reconstituted in 3 ml media. LPS treated DCs are counted and reconstituted in media as per assay requirement.

Preparation of PBLs:
Following the same protocol as mentioned before, Ficoll separation is performed after collecting blood from another healthy individual. After monocyte depletion the non adhered cells (PBLs) are collected and spun down @ 1500 rpm for 5 minutes and reconstituted in 5 ml media. PBLs are counted and reconstituted to $1.0 \times 10^6$ cells/ml.

SEB Treatment to Dendritic Cells:
Preparation of SEB: SEB stock concentration is 1 mg/ml. From the stock 3 µl of SEB is dissolved in 3 ml of media to get 1 ug/ml working solution of SEB. Treatment: As per the standardized protocol $0.06 \times 10^6$ DCs are treated with 0.6 µg of SEB. A stock $0.1 \times 10^6$ cells/ml (LPS treated matured DCs) is made. From this, 600 µl of cell suspension is dissolved in 2.4 ml of assay media (total volume of cell suspension is 3 ml that contains $0.02 \times 10^6$ cells/ml). This is spun down @ 1500 rpm for 5 min and 600 µl of SEB (1 ug/ml) is added to the pellet. This is incubated inside $CO_2$ incubator @ 37° C. for 20 minutes. Excess media (2 ml) is added to the tube after incubation and washed @ 1500 rpm for 5 min. Supernatant is discarded and the cells are washed again with 3 ml of media. Finally the pellet is dissolved in 3 ml of assay media.

Mytomycin C Treatment to PBLs:
25 µg/ml mytomycin solution is made from the mytomycin stock of 1 mg/ml. $0.5 \times 10^6$ PBLs are treated with 500 µl of 25 µg/ml Mytomycin for 30 min inside $CO_2$ incubator @ 37° C. Excess media (2 ml) is added to it after the incubation and the cells are washed @ 1500 rpm for 5 media. Supernatant is discarded and the cells are washed again with 3 ml of media.

MLR Assay—Inhibition of Proliferation:
MLR assay is performed at DC:PBL=1:50 ratio. Negative control used is Nimotuzumab. After 6 days the plate is read with alamar blue. Supernatant from a parallel plate is taken and assayed for cytokines using a Th1, Th2 and Th17 CBA human kit (BD biosciences, Pharmingen, USA) is used as per the manufacturer's instruction. Concentration of cytokines is determined from a standard supplied along with the kit. All samples were analysed with a Cyan—ADP, Beckman Coulter, Flow cytometer with the Summit 4.3 Software.

Results: Significant difference in the key cytokines evaluated is observed in the presence of Itolizumab as compared to control (Nimotuzumab) treated group. The mean Th17 determining cytokine, IL17 is reduced almost 50%.

Example 2

Induction of EAE and Treatment:
Mice were immunized subcutaneously on day 0 with 200 µl of emulsion consisting of 20 µg of MOG 35-55 in PBS combined with an equal volume of CFA containing 500 µg heat-killed *M. tuberculosis* H37Ra. The emulsion was injected in one of lower dorsum and followed by an intravenous injection of 100 µl of *B. pertussis* toxin (0.2 µg/100 µl) in 0.01M PBS through lateral tail vein. The booster dose of 100 µl of *B. pertussis* toxin was given on day 3. Mice were re-immunized on day 7 with 200 µl of MOG/CFA emulsion injected subcutaneously on the other flank. On day 14 mice were randomized and grouped as control and anti CD6 treated mice. Treated group of mice were injected with anti-mouse CD6 MAb (R&DSystem)/10D12 60 ug/100 ul/dose, intraperitoneally on every alternate day. Control mice were injected with same dose of anti-rat IgG MAb. Mice were observed for symptoms of EAE. Disease severity and onset in control and treated group was scored as clinical score from day 14 to 32 on a 5 point scale as—0, normal; 0.5, stiff tail; 1, limp tail; 1.5, limp tail with inability to right; 2, paralysis of one limb; 2.5 paralysis of one limb and weakness of one other limb; 3, complete paralysis of both hind limbs; 4 moribund; 5, death. Mean clinical score was calculated by adding the clinical scores for one group and dividing by the total number of mice in that group. The induction of disease in mice was more than 95%.

T Cell Receptor (CD3) Mediated Proliferation Assay

Mice were sacrificed on day 30. Spleen and blood was assessed from each mouse. Spleens obtained from same group of mice were pooled for in vitro experiments. Splenocytes ($0.2 \times 10^6$ cells/well) obtained from MOG immunized; control and antiCD6 MAb treated mice were stimulated with precoated antiCD3 MAb (2.5 µg/ml) in 96 well plates (Nunc). Splenocytes in uncoated wells were used as unstimulated control cells. Cells were incubated for 3 days. On day 3 alamar blue (30 al/well; Invitrogen) was added. After overnight incubation plates were read at 530/590 nm using Biotek Synergy plate reader next morning. Data was represented as mean Relative fluorescence unit (RFU) values from unstimulated and stimulated splenocytes of both the groups Cytokine Analysis For cytokine analysis same set up of proliferation assay was used for stimulation of splenocytes. Briefly, splenocytes ($0.2 \times 10^6$ cells/well) obtained from MOG immunized; control and antiCD6 MAb treated mice were stimulated with precoated antiCD3 MAb (2.5 µg/ml) in 96 well plates (Nunc). Splenocytes in uncoated wells were used as unstimulated control cells. On day 3 supernatants were collected and preserved at −80° C. until cytokine measurement was performed using Cytometeric bead array (CBA) inflammatory cytokine kit (Interleukin-6, Interleukin-10, Interleukin-12p70, Interferon-γ, Tumor Necrosis Factor-α) (BD Biosciences, USA) as per manufacturer's instructions. Briefly, 50 µl of mixed bead population with discrete fluorescence intensities and coated with cytokine specific capture antibodies was added to 50 µl of supernatant, and 50 µl of phycoerythrin detection reagent for inflammatory cytokine antibodies. Simultaneously, standards for each cytokine (0-5000 pg/ml) were likewise mixed with cytokine capture beads and phycoerythrin detection n reagent. The vortexed mixtures were allowed to incubate for 2 hrs at room temperature in dark. Beads were washed and acquired on flow cytometer (CyAnDMADP, Dako). Standard curves were derived from the cytokine standards supplied with the kit and quantity (pg/ml) of respective cytokine was calculated using standard graphs.

For detection of Interleukin-17A flex set assay kit (BD Biosciences, USA) was used as per manufacturer's instructions. Briefly, 50 µl of capture bead solution coated with IL-17A specific capture antibodies was added to 50 µl of supernatant or standard (0-5000 pg/ml) and incubated for 1 hr at room temperature. Beads were washed and incubated with 50 µl of phycoerythrin detection reagent for 1 hr at room temperature. Beads were washed and acquired on flow cytometer (CyAnDMADP, Dako). Standard curve was derived from the cytokine standards supplied with the kit and quantity (pg/ml) of IL-17A was calculated using standard graph.

Results: Mice treated with anti-mouse CD6 antibody showed significant clinical improvement over the Rat antibody treated group. Statistically significant difference in the anti mouse CD6 treated group as compared to the control Rat IgG treated group was observed for the following cytokines TNFα, IL6, IFNγ and IL17.

Example 3

Method

1. Human PBMC Culture for Th17 Polarization

Human blood was collected from healthy volunteers after signing an informed consent form and PBMCs (peripheral blood mononuclear cells) were separated by standard density gradient centrifugation over Ficoll Paque (GE Healthcare Bio-sciences AB, Uppsala, Sweden). PBMCs were counted and plated in 96 well flat bottom plates, at a density of 0.1 million cells per well and stimulated with anti-CD3/anti-CD28 coated beads (each antibody coated on beads at a final concentration of 5 ng for 0.1 million cells per well) under non-polarizing (Thnp) and Th17 polarizing conditions (Th17pol). In Th17pol conditions, polarizing cytokines and growth factors were added at a final concentration of: IL-1β 10 ng/mL, IL-6 10 ng/mL, TGF-β15 ng/mL, IL-23 10 ng/mL, anti-IL-4 10 µg/mL and anti-IFN-γ 2.5 µg/mL. Itolizumab or irrelevant isotype control antibody (control) were added to cells in both Thnp and Thpol conditions at a final concentration of 40 µg/mL. Cells were cultured in a 37° C. $CO_2$ incubator for 13 days and sampled at various time points (day 3, day 6, day 8 and day 13) for cytokines, cell-surface and intracellular marker analysis. For cells that were continuously cultured, 50 µL medium was replaced with RPMI complete medium containing 2 ng/mL IL-2 for Thnp condition and 2 ng/mL IL-2 along with 10 ng/ml IL-23 for Th17pol condition on days 6 and 10.

2. Cytokine Analysis

At each time point, 100 µL of cell supernatant was collected and pooled from quadruplicate wells and frozen at −80° C. Cytokine analysis was performed as per manufacturer instructions using Human IFN-γ Quantikine SixPak (SIF50) and Human IL-17 (IL-17A) (Quantikine SixPak (S1700) kits from R&D Systems. Absorbance was read at 450/630 nm using SpectraMax M5$^e$ reader, Molecular Devices, Sunnyvale, Calif., USA.

3. Flow Cytometry Analysis

Cell surface marker staining: At each time point, cells from quadruplicate wells were harvested and blocked with Human Fc receptor binding inhibitor and incubated at 4° C. for 30 minutes. Cells were centrifuged and re-suspended in staining buffer (2% FBS in 1×PBS) containing the antibodies for cell surface markers (e.g. CD4, CD8, CD25, CD6). Acquisition and analysis of samples were performed using a Cyan-ADP flow cytometer with the Summit version 4.3 software (Beckman Coulter, Fullerton, Calif., USA). Lymphocytes were gated by forward and side scatter and further gated on CD4$^+$T cells.

4. Statistical Analyses

GraphPad Prism 6.0 software (GraphPad software, San Diego, Calif., USA) was used for all statistical analysis. Statistical significance was determined using unpaired t test followed by Holm-Sidak method, with alpha=5.000% (FIG. 3B).

Results:

T Cell Activation and CD6 Overexpression in Th17 Polarizing Conditions.

As shown in FIG. 3A, by day 13 the increase in secreted IL-17 levels was 3-4 fold higher than the rise in IFN-γ release in cells stimulated in Th17pol conditions (PBMCs stimulated with anti-CD3/anti-CD28 in presence of Th17 polarizing, Th17pol, cytokines) as compared to Thnp cells (PBMCs stimulated with anti-CD3/anti-CD28, Non-Polarizing condition; Thnp). Absolute concentrations of IL-17 and IFN-γ on day 13 are shown in FIG. 3B. IFN-γ released by cells stimulated in Th17pol condition was significantly low as compared to the Thnp cells. Similarly these Th17pol cells showed a 3-4 fold increase in secreted IL-17 levels as compared to Thnp cells. These results indicate that under Th17pol conditions a shift towards Th17 cells was initiated as early as day 3 with full establishment by day 13. There was similar activation of CD4$^+$T cells on day 3, as indicated by CD25 (IL-2Rα) over expression in Thnp as well as Th17pol conditions (FIG. 3C).

The surface expression of CD6 receptors on CD4$^+$T cells increased after 48 hours of stimulation and was sustained till day 12/13, the end of the polarizing experiment. Representative analysis on day 9, as histogram overlay for CD6 expression on CD4$^+$T cells for one donor is shown in FIG. 3D. Biotinylated Itolizumab (anti-human CD6) as a detection reagent, identified CD6 overexpression in 15-30% and 25-35% of CD4$^+$T cells in Thnp and Th17pol conditions respectively (FIG. 3D). As shown in FIG. 3E (data from 6 different donors), Thnp and Th17pol CD4$^+$T cells showed consistent increase in CD6 MFI over the unstimulated cells. Increase in CD6 expression was also confirmed with the use of commercially available domain1 binding anti-CD6 antibodies (MEM98 and MT605 clones FIG. 3E). The increase in CD6 MFI in Th17pol over Thnp cells (FIGS. 3D and E) are in line with the reports from clinical sample derived clones of Th17 cells overexpressing CD6 as compared to Th1 cells (Brucklacher-Waldert, Stuerner et al. 2009). This overexpression was not only limited to CD4$^+$T cells but was also observed in activated CD8$^+$T cells.

Example 4

Method

1. Human PBMC Culture for Th17 Polarization:

Same as described in Example 3. The experiment was carried out only till day 3 and day 6 in this particular case.

2. CFSE Labelling and T Cell Proliferation Assay

PBMCs were incubated with CFSE dye at a final concentration of 5 µM, incubated at 37° C., $CO_2$ incubator for 15 minutes (with intermittent shaking), centrifuged and resuspended in complete medium and again incubated at 37° C., $CO_2$ incubator for 30 minutes for the stabilization. Cells were washed and stimulated in Thnp and Th17pol conditions with control or Itolizumab antibody. On day 3 post stimulations cells were analysed for CFSE dilution on CD4$^+$T cells using flow cytometry.

3. Flow Cytometry Analysis

Cell Surface Marker Staining:

At each time point, cells from quadruplicate wells were harvested and blocked with Human Fc receptor binding inhibitor and incubated at 4° C. for 30 minutes. Cells were centrifuged and re-suspended in staining buffer (2% FBS in 1×PBS) containing the antibodies for cell surface markers (e.g. CD4, CD8, CD25). Acquisition and analysis of samples were performed using a Cyan-ADP flow cytometer with the Summit version 4.3 software (Beckman Coulter, Fullerton, Calif., USA). Lymphocytes were gated by forward and side scatter and further gated on CD4$^+$T cells.

Results:

Itolizumab is Associated with Inhibition of T Cell Activation and Proliferation in Thnp and Th17Pol Conditions.

We had previously reported a 50-55% decrease in CD25 expression on anti-CD3 as well as anti-CD3 and ALCAM co-stimulated cells in the presence of Itolizumab (Nair, Melarkode et al. 2010). Here, we show that, there is significant reduction in CD25 expression on stimulated CD4$^+$T cells (~50% reduction) in Thnp and Th17pol conditions in presence of Itolizumab (FIG. 4A). This would imply that the antibody in various contexts of stimulation is able to consistently and similarly inhibit the activation of T cells.

Similar to inhibition of activation of T cells, we observed that Itolizumab also inhibited the proliferation of T cells. In presence of Itolizumab, a significant reduction in CD4$^+$T cell proliferation (~38% in Thnp and ~62% reduction in Th17pol condition) was observed (indicated by reduced number of CFSE lo cells) confirming the inhibitory role of Itolizumab in T cell activation and proliferation (FIG. 4B).

Example 5

Method:

1. Human PBMC Culture for Th17 Polarization:

Same as described in Example 3

2. Flow Cytometry Analysis

Intracellular cytokine staining for IL-17A and IFN-γ was performed as follows. At the time point of analysis, cells were left unstimulated or stimulated with 50 ng/mL of PMA and 1 µg/mL of ionomycin in presence of BD Golgi Stop Plug™ and incubated for 5 hours at 37° C. Cells were harvested and washed in staining buffer and blocked with human Fc receptor binding inhibitor. After surface marker staining, cells were re-suspended in BD Cytofix/Cytoperm™ fixation/permeabilization buffer, and intracellular staining was performed as per manufacturer instructions. Acquisition and analysis of samples were performed using a Cyan-ADP flow cytometer with the Summit version 4.3 software (Beckman Coulter, Fullerton, Calif., USA). Lymphocytes were gated by forward and side scatter and further gated on CD3$^+$T cells as mentioned in the respective experiments.

3. Cytokine Analysis

At each time point, 100 µL of cell supernatant was collected and pooled from quadruplicate wells and frozen at −80° C. Cytokine analysis was performed as per manufacturer instructions using Human IFN-γ Quantikine SixPak (SIF50) and Human IL-17 (IL-17A) (Quantikine SixPak (S1700) kits from R&D Systems. Absorbance was read at 450/630 nm using SpectraMax M5$^e$ reader, Molecular Devices, Sunnyvale, Calif., USA.

4. Statistical Analyses

GraphPad Prism 6.0 software (GraphPad software, San Diego, Calif., USA) was used for all statistical analysis. Statistical significance was determined using unpaired t test followed by Holm-Sidak method, with alpha=5.000% (FIGS. 5 D and E).

Results:

Itolizumab is Associated with Reduction in Th17 Hallmark Cytokines

Under Th17pol conditions intracellular expression of Th1 (IFN-γ) and Th17 (IL-17A) signature cytokines were compared between control antibody and Itolizumab treated cells. Representative dot plot from day 6, show only minimal expression of both IFN-γ and IL-17A upon Itolizumab treatment, as compared to controls (FIG. 5A). Similar reductions, with Itolizumab treatment were also observed in Thnp conditions.

The time course study across days 3, 6, 8 and 13 demonstrated maximum decrease in intracellular IFN-γ on days 6 and 8 (FIG. 5B). Similarly, maximum inhibition (80-90%) of intracellular IL-17A by Itolizumab was also observed on these days (FIG. 5C). A corresponding correlation and decrease in IFN-γ and IL-17 release, upon Itolizumab treatment (as evaluated by measuring secreted cytokines) was also observed (FIGS. 5D and E). The similar pattern of inhibition for both the intracellular cytokines measured as well as the secreted cytokines confirmed the effect of Itolizumab in these two major effector Th subsets.

Example 6

Method:
1. Human PBMC Culture for Th17 Polarization:
Same as described in Example 3
2. Flow Cytometry Analysis Intracellular staining for pSTAT3 was performed as follows. At the time point of analysis cells were harvested and washed in staining buffer and blocked with human Fc receptor binding inhibitor. After surface marker (CD4) staining, cells were fixed with 2% PFA (100 µl for each staining well) and incubated at 4° C. for 15-20 mins. Cells were washed with PBS, twice and permeabilised with 100% chilled methanol. 500 µl of chilled methanol was added while gently vortexing the cells and were incubated at 4° C. for 20 mins. After centrifugation, at 4° C. at ~250×g for 5 mins methanol was decanted and cells were resuspended in staining buffer. Antibodies for intracellular staining were diluted in staining buffer and added at appropriate dilutions and plates were incubated at 4° C. for 30 minsCells were washed thrice in staining buffer and resuspended in 1×PBS and acquired (all washes done at 4° C.).

Intracellular cytokine staining for IL-17A and transcription factor RORγT was performed as follows. At the time point of analysis, cells were left unstimulated or stimulated with 50 ng/mL of PMA and 1 µg/mL of ionomycin in presence of BD Golgi Stop Plug™ and incubated for 5 hours at 37° C. Cells were harvested and washed in staining buffer and blocked with human Fc receptor binding inhibitor. After surface marker (CD3) staining, cells were re-suspended in BD Cytofix/Cytoperm™ fixation/permeabilization buffer, and intracellular staining was performed as per manufacturer instructions.

Intracellular cytokine staining for IL-17A and surface marker CCR6 and CD3 was performed as follows. At the time point of analysis, cells were left unstimulated or stimulated with 50 ng/mL of PMA and 1 µg/mL of ionomycin in presence of BD Golgi Stop Plug™ and incubated for 5 hours at 37° C. Cells were harvested and washed in staining buffer and blocked with human Fc receptor binding inhibitor. After surface marker (CD3 and CCR6) staining, cells were re-suspended in BD Cytofix/Cytoperm™ fixation/permeabilization buffer, and intracellular staining was performed as per manufacturer instructions Acquisition and analysis of samples were performed using a Cyan-ADP flow cytometer with the Summit version 4.3 software (Beckman Coulter, Fullerton, Calif., USA). Lymphocytes were gated by forward and side scatter and further gated on $CD4^+$ or $CD3^+$T cells as mentioned in the respective panels.

Results:
Reduction in Signature Th17 Specific Markers in Presence of Itolizumab

Th17 differentiation involves the synergistic combination of pSTAT3 and RORγT transcription factors (Annunziato, Cosmi et al. 2007; Bettelli, Korn et al. 2008; de Wit, Souwer et al. 2011). Previously we have reported on Itolizumab mediated reduction in pSTAT3 expression on activated T cells (Nair, Melarkode et al. 2010) which was further confirmed in the present study (FIG. 6A). We also show, in Th17pol conditions there is a substantial reduction in IL-17A and RORγT double positive T cells in the presence of Itolizumab as compared to control antibody treated cells. Correlating with the peak inhibition of effector cytokines (FIG. 5B-E), the inventors observe a substantial reduction in these double positive cells (70-80% reduction) and total RORγT MFI on day 6 (FIGS. 6B and 6C respectively). Similar trend was also observed on day 8.

CCR6 is the signature surface marker for Th17 cells (Liu and Rohowsky-Kochan 2008; Singh, Zhang et al. 2008). Therefore it was of interest to evaluate CCR6 expression in IL-17 producing T cells and effect of Itolizumab on them. As analysed on day 6, in Th17pol conditions, 50-60% reduction in the expression of $CCR6^+IL-17A^+$ (dual positive) $CD3^+T$ cells was observed in the presence of Itolizumab as compared to the control (FIG. 6D). Similar reductions were also observed on day 10.

While $CCR6^+T$ cells are either memory or Treg cells (Yamazaki, Yang et al. 2008) all these cells are not IL-17 producing Th17 cells (Sallusto, Lenig et al. 1998; Liao, Rabin et al. 1999; Kleinewietfeld, Puentes et al. 2005). Itolizumab had little impact on the $IL-17^-CCR6^+$ (non-Th17 cells). This observation is distinct from the decrease observed in total RORγT MFI in the presence of Itolizumab as compared to the control (FIG. 6C), suggesting that Itolizumab could down regulate the expression of transcription factor RORγT but affects only the $IL17^+$ subset of CCR6 expression T cells. These experiments prove that Itolizumab inhibits the activation and differentiation of Th17 cells by inhibiting key transcription factors pSTAT3, RORγT along with $RORγT^+$ $IL-17A^+$ and $CCR6^+IL-17^+T$ cells (FIG. 6) across days.

REFERENCES

Annunziato, F., L. Cosmi, et al. (2007). "Phenotypic and functional features of human Th17 cells." *J Exp Med* 204(8): 1849-61.
Bettelli, E., T. Korn, et al. (2008). "Induction and effector functions of T(H)17 cells." *Nature* 453(7198): 1051-7.
Brucklacher-Waldert, V., K. Stuerner, et al. (2009). "Phenotypical and functional characterization of T helper 17 cells in multiple sclerosis." *Brain* 132(Pt 12): 3329-41.
De Wit, J., Y. Souwer, et al. (2011). "CD5 costimulation induces stable Th17 development by promoting IL-23R expression and sustained STAT3 activation." *Blood* 118 (23): 6107-14.
Kleinewietfeld, M., F. Puentes, et al. (2005). "CCR6 expression defines regulatory effector/memory-like cells within the CD25(+)CD4+ T-cell subset." *Blood* 105(7): 2877-86.
Liao, F., R. L. Rabin, et al. (1999). "CC-chemokine receptor 6 is expressed on diverse memory subsets of T cells and determines responsiveness to macrophage inflammatory protein 3 alpha." *J Immunol* 162(1): 186-94.
Liu, H. and C. Rohowsky-Kochan (2008). "Regulation of IL-17 in human CCR6+ effector memory T cells." *J Immunol* 180(12): 7948-57.

Nair, P., R. Melarkode, et al. (2010). "CD6 synergistic co-stimulation promoting proinflammatory response is modulated without interfering with the activated leucocyte cell adhesion molecule interaction." *Clin Exp Immunol* 162(1): 116-30.

Sallusto, F., D. Lenig, et al. (1998). "Flexible programs of chemokine receptor expression on human polarized T helper 1 and 2 lymphocytes." *J Exp Med* 187(6): 875-83.

Singh, S. P., H. H. Zhang, et al. (2008). "Human T cells that are able to produce IL-17 express the chemokine receptor CCR6." *J Immunol* 180(1): 214-21.

Yamazaki, T., X. O. Yang, et al. (2008). "CCR6 regulates the migration of inflammatory and regulatory T cells." J Immunol 181(12): 8391-401.

What is claimed is:

1. A method of treatment for multiple sclerosis in a subject, wherein the subject in need of such treatment exhibits an increased number of T helper 17 (Th17) cells when compared to a healthy subject, the method comprising:
    administering a humanized antibody that specifically binds to D1 of CD6 of the subject and causes a reduction of expression of IL-23R on one or more of monocytes, T helper cells and natural killer cells in a body fluid of the subject, wherein the humanized antibody is the only therapeutic antibody administered; and monitoring IL-23R expression on blood cells and/or dendritic cells of the subject.

2. The method of claim 1, wherein the subject in need of such treatment also exhibits an increased number of T helper 1 (Th1) cells when compared to a healthy subject.

3. The method of claim 1, wherein the humanized antibody is Itolizumab.

4. The method of claim 3, wherein the humanized antibody causes a reduction of one or more of TNF-alpha, IFN-gamma, IL-6, and IL-17A in a body fluid of the subject.

5. A method of treatment for multiple sclerosis in a subject experiencing an increase in T helper 17 (Th17) cells and T helper 1 (Th1) cells, the method comprising:
    administering Itolizumab a humanized antibody that specifically binds to CD6 to the subject, wherein the humanized antibody is the only therapeutic antibody administered; and monitoring IL-23R expression on blood cells and/or dendritic cells of the subject, wherein the treatment causes a reduction of expression of IL-23R and subsequent reduction of Th1 cells and Th17 cells.

6. The method of claim 5, wherein the Itolizumab causes a reduction of one or more of TNF-alpha, IFN-gamma, IL-6, and IL-17A in a body fluid of the subject.

* * * * *